(12) United States Patent
Gibler et al.

(10) Patent No.: US 10,195,350 B2
(45) Date of Patent: Feb. 5, 2019

(54) SEALING ARRANGEMENT FOR SYRINGE

(75) Inventors: Martin J. Gibler, West Chester, OH (US); Mark A. Bennett, Loveland, OH (US); Kenneth R. Waeber, Milford, OH (US); Kenneth E. Hogue, Chapel Hill, NC (US); Christoph L. Gillum, Middletown, OH (US); Patrick A. Harrell, Loveland, OH (US); David A. Parrott, Cincinnati, OH (US); Sean E. Mackey, Grayslake, IL (US); Rajkumar V. Conjeevaram, Lake Bluff, IL (US); Thomas Rebne, Woodstock, GA (US); Bradley A. Clark, High Point, NC (US); Jeremy L. Hemingway, Cincinnati, OH (US); Ji Zhou, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 288 days.

(21) Appl. No.: 13/600,060

(22) Filed: Aug. 30, 2012

(65) Prior Publication Data

US 2013/0102994 A1 Apr. 25, 2013

Related U.S. Application Data

(60) Provisional application No. 61/684,015, filed on Aug. 16, 2012, provisional application No. 61/562,275, (Continued)

(51) Int. Cl.
*A61M 5/315* (2006.01)
*A61M 5/145* (2006.01)
(Continued)

(52) U.S. Cl.
CPC ...... *A61M 5/31505* (2013.01); *A61M 5/1452* (2013.01); *A61M 5/31513* (2013.01);
(Continued)

(58) Field of Classification Search
CPC ...... A61M 5/002; A61M 5/178; A61M 5/315; A61M 5/31505; A61M 5/31501;
(Continued)

(56) References Cited

U.S. PATENT DOCUMENTS 2,895,773 A * 7/1959 McConnaughey ............ A61M 5/31513
277/437
4,201,209 A 5/1980 Leveen et al.
(Continued)

FOREIGN PATENT DOCUMENTS

DE 102008058034 A1 5/2010
EP 0511402 A1 11/1992
(Continued)

OTHER PUBLICATIONS

International Search Report and Written Opinion for Application No. PCT/US2012/053218, dated Feb. 28, 2013, 7 pages.
(Continued)

*Primary Examiner* — Bradley J Osinski
*Assistant Examiner* — Nilay Shah
(74) *Attorney, Agent, or Firm* — McCarter & English, LLP; David R. Burns

(57) ABSTRACT

A syringe containing a high water content product and for use in a drug infusion system is provided. The syringe includes a plunger carrying front and rear o-rings made of a diene rubber compound such as chlorobutyl rubber or bromobutyl rubber to impart very low gas permeability characteristics to the o-rings. The plunger may be molded as a single part or in two parts. If molded as one part with radially-engaging mold portions, the seal glands in the plunger may include parting lines from the mold. If molded as two parts with axially-engaging mold portions, the front seal gland may include a sealing surface and under cut that
(Continued)

has no parting line. The o-rings may be surface treated with a lubricant to improve sealing where the molding process gives rise to parting lines in the seal glands.

16 Claims, 23 Drawing Sheets

Related U.S. Application Data filed on Nov. 21, 2011, provisional application No. 61/529,718, filed on Aug. 31, 2011.

(51) Int. Cl.
*B65B 1/04* (2006.01)
*A61M 5/31* (2006.01)

(52) U.S. Cl.
CPC ............ *B65B 1/04* (2013.01); *A61M 5/315* (2013.01); *A61M 2005/3117* (2013.01); *A61M 2205/0222* (2013.01)

(58) Field of Classification Search
CPC ........ A61M 5/31566; A61M 5/315066; A61M 5/5066; A61M 5/31515
See application file for complete search history.

(56) References Cited

U.S. PATENT DOCUMENTS

| | | | |
|---|---|---|---|
| 4,303,070 A | 12/1981 | Ichikawa et al. | |
| 4,439,184 A | 3/1984 | Wheeler | |
| 4,632,672 A | 12/1986 | Kvitrud | |
| 4,692,156 A * | 9/1987 | Haller | A61M 5/322 600/576 |
| 4,713,060 A * | 12/1987 | Riuli | A61M 5/002 604/199 |
| 5,226,881 A * | 7/1993 | Pickhard | A61M 5/5066 604/110 |
| 5,338,309 A | 8/1994 | Imbert | |
| 5,397,313 A | 3/1995 | Gross | |
| 5,435,075 A | 7/1995 | Shiraishi et al. | |
| 5,435,076 A | 7/1995 | Hjertman et al. | |
| 5,549,573 A | 8/1996 | Waskönig | |
| 5,637,100 A | 6/1997 | Sudo | |
| 5,902,276 A | 5/1999 | Namey, Jr. | |
| 6,224,577 B1 * | 5/2001 | Dedola | A61M 5/31513 604/218 |
| 7,547,297 B2 | 6/2009 | Brinkhues et al. | |
| 7,927,315 B2 | 4/2011 | Sudo et al. | |
| 8,096,971 B2 | 1/2012 | Bassarab et al. | |
| 9,669,165 B2 | 6/2017 | Mackey et al. | |
| 2001/0041867 A1 | 11/2001 | Schottli | |
| 2002/0165496 A1 | 11/2002 | Thompson | |
| 2003/0097096 A1 * | 5/2003 | Niedospial, Jr. | 604/218 |
| 2003/0212368 A1 | 11/2003 | Shue et al. | |
| 2004/0054332 A1 | 3/2004 | Ferguson | |
| 2004/0141886 A1 | 7/2004 | Py et al. | |
| 2005/0148932 A1 | 7/2005 | Rimlinger et al. | |
| 2005/0154353 A1 * | 7/2005 | Alheidt | A61M 5/31515 604/218 |
| 2005/0197626 A1 | 9/2005 | Moberg et al. | |
| 2006/0178643 A1 * | 8/2006 | Sudo et al. | 604/230 |
| 2008/0264261 A1 * | 10/2008 | Kavazov | A61J 1/2096 96/193 |
| 2008/0300550 A1 * | 12/2008 | Schiller | A61M 5/31511 604/220 |
| 2009/0099512 A1 | 4/2009 | Digregorio et al. | |
| 2009/0166978 A1 * | 7/2009 | Hoffmann | A61M 5/31513 277/437 |
| 2009/0326458 A1 * | 12/2009 | Chong et al. | 604/152 |
| 2010/0022990 A1 | 1/2010 | Karpowicz et al. | |
| 2010/0042055 A1 | 2/2010 | Sudo et al. | |
| 2010/0163574 A1 | 7/2010 | Digregorio et al. | |
| 2011/0101563 A1 | 5/2011 | Costa et al. | |
| 2011/0152820 A1 | 6/2011 | Chattaraj et al. | |
| 2013/0126559 A1 * | 5/2013 | Cowan | A61M 5/31525 222/333 |
| 2017/0189620 A1 | 7/2017 | Mackey et al. | |

FOREIGN PATENT DOCUMENTS

| | | |
|---|---|---|
| EP | 0960616 A2 | 12/1999 |
| EP | 1488818 A1 | 12/2004 |
| WO | 9215350 A1 | 9/1992 |
| WO | 2001/23017 A2 | 4/2001 |
| WO | 2002/30494 A2 | 4/2002 |
| WO | 2004004811 A1 | 1/2004 |
| WO | 2006/056452 A1 | 6/2006 |
| WO | 2007/005902 A2 | 1/2007 |
| WO | 2009001600 A1 | 12/2008 |
| WO | 2009061884 A1 | 5/2009 |
| WO | 2009119496 A1 | 10/2009 |

OTHER PUBLICATIONS

European Office Action for Application No. 12762454.2, dated Mar. 23, 2017. 5 pages.
European Office Action for Application No. 12762454.2, dated Nov. 27, 2017. 5 pages.
International Search Report and Written Opinion for Application No. PCT/US2013/031750, dated May 21, 2014.
Invitation to Pay Additional Fees for Application No. PCT/US2013/031750, dated Jan. 7, 2014.

* cited by examiner

SEALING ARRANGEMENT FOR SYRINGE

This application claims priority to U.S. Provisional Application No. 61/529,718 filed Aug. 31, 2011, to U.S. Provisional Application No. 61/562,275 filed Nov. 21, 2011, and to U.S. Provisional Application No. 61/684,015 filed Aug. 16, 2012, the contents of all of the foregoing provisional applications being incorporated herein by reference.

BACKGROUND

The present invention relates to a sealing arrangement for the plunger of a syringe used in a drug infusion system.

SUMMARY

The invention provides a syringe for use in a drug infusion system, the syringe comprising: a barrel having a front end, a rear end, and a cylindrical wall defining an outer surface and an inner surface, the rear end being open, and the front end including an orifice; a plunger within the barrel, the plunger including a contact surface at a front end of the plunger, and a front seal gland extending circumferentially around the plunger; a front o-ring made of a diene rubber compound, positioned in the front seal gland, and creating a gas-tight seal between the inner surface of the barrel and the plunger; wherein a product chamber is defined between the inner surface of the barrel, the front o-ring, and contact surface; wherein the product chamber is adapted to contain a product to be dispensed by the syringe; wherein actuation of the plunger within the barrel decreases the volume of the product chamber to dispense the product through the orifice; and wherein the front o-ring is sized to maintain the gas tight seal through a temperature range of $-25°$ C. to $40°$ C.

In some embodiments, the front o-ring is surface treated with a lubricant to ensure a gas-tight seal between the front o-ring and the front seal gland. In some embodiments, the syringe further comprises: a rear seal gland axially spaced to the rear of the front seal gland and extending circumferentially around the plunger; a rear o-ring made of a diene rubber compound; wherein the rear o-ring is positioned in the rear seal gland; and wherein the rear o-ring creates a gas-tight seal between the inner surface of the barrel and the plunger. In some embodiments, a front end of the plunger defines a head that includes the contact surface; wherein an outer diameter of the head is slightly smaller than an inner diameter of the barrel such that the head fits within the barrel with close tolerances; wherein a rear end of the plunger includes an integrally-formed molded ring having a maximum outer diameter that is slightly less than an inner diameter of the barrel such that the integrally-formed molded ring fits within the barrel with close tolerances; and wherein the head and integrally-formed molded ring resist tipping of the plunger within the barrel. In some embodiments, the front o-ring is sized to maintain the gas tight seal through a temperature range of $-20°$ C. to $40°$ C. In some embodiments, the plunger is molded as a single piece; wherein the front seal gland includes a parting line arising from the molding process; wherein the seal between the front o-ring and the front seal gland includes a leak path arising from the parting line; and wherein the front o-ring is surface treated with a lubricant to gas-tightly seal the leak path. In some embodiments, the plunger is molded as a front portion and a rear portion; wherein the front portion is molded with axially-engaging mold portions to form a portion of the front seal gland with no parting lines; and wherein the rear portion is molded with radially-engaging mold portions to form a portion of the front seal gland with parting lines; and wherein the front o-ring is received within in the front seal gland with no leak paths between the o-ring and the portion of the front seal gland having no parting lines.

In some embodiments, the front seal gland includes a rear-facing undercut surface in front of the o-ring; wherein a pocket is defined between the o-ring and the rear-facing undercut surface of the front seal gland; and wherein the plunger includes a venting slot in the rear-facing undercut surface, the venting slot communicating between the pocket and the product chamber such that air in the pocket is evacuated through the venting slot when a vacuum is applied to the product chamber. In some embodiments, the pocket is an annular pocket extending around the entire circumference of the front seal gland; wherein the venting slot includes two diametrically opposed venting slots communicating with the annular pocket. In some embodiments, the syringe further comprises a deflectable tab in the plunger and an insert that deflects the deflectable tab radially outwardly; wherein the deflectable tab, when deflected outwardly by the insert, bears against the inner surface of the barrel to prevent tipping of the plunger in the barrel. In some embodiments, the deflectable tab includes a plurality of deflectable tabs; and wherein the insert includes a ring-shaped insert that expands all deflectable tabs radially outwardly. In some embodiments, the plunger further includes a flexible wiper that engages the inner surface of the barrel to prevent tipping of the plunger in the barrel. In some embodiments, the flexible wiper is integrally formed with the plunger. In some embodiments, the plunger further includes a circumferential slot; and wherein the wiper is inserted into the circumferential slot and extends radially outwardly into contact with the barrel inner surface.

The invention also provides a method for storing and dispensing a product having a high content of water, the method comprising: providing a syringe barrel having a front end, a rear end, and a cylindrical wall defining an outer surface and an inner surface, the rear end being open, and the front end including an orifice; providing a plunger having a contact surface at a front end of the plunger, and a front seal gland extending circumferentially around the plunger; forming a front o-ring of a diene rubber compound; positioning the front o-ring in the front seal gland to define a plunger and front o-ring assembly; inserting the plunger and front o-ring assembly into the barrel such that the front o-ring is deflected between the inner surface of the barrel and the plunger to create a sliding gas-tight seal between the inner surface of the barrel and the plunger; defining a product chamber between the inner surface of the barrel, the front o-ring, and contact surface; filling the product chamber with the product having high water content; freezing the product-filled syringe at a temperature at least as low as $-20°$ C.; in response to freezing the product-filled syringe, changing the phase of the water content of the product to ice, resulting in expansion of the product within the syringe; in response to expansion of the product within the syringe, displacing the plunger within the barrel to expand the volume of the product chamber to accommodate the product expansion, while maintaining the gas-tight seal between the front o-ring and the contact surface; storing the frozen product-filled syringe until an approximate time of use; at the approximate time of use, thawing the frozen product-filled syringe to a temperature of at least $2°$ C. to $40°$ C.; in response to thawing of the frozen product-filed syringe, changing the phase of the water content of the water to liquid; in response to changing the phase of the water content to liquid, contracting the product; in response to contracting the product, developing vacuum bubbles within the product, thereby giving rise to a vacuum force on the plunger that is the product of the vacuum pressure and a surface area of the contact surface; in response to the vacuum pressure, moving the plunger within the barrel to reduce the volume of the product chamber to accommodate a decreased volume occupied by the product while maintaining the gas-tight seal; and actuating the plunger to decrease the volume of the product chamber and thereby dispense the thawed product from the syringe through the orifice.

In some embodiments, the method further comprises the step of surface treating the front o-ring with a lubricant to ensure a gas-tight seal between the front o-ring and the front seal gland. In some embodiments, the method further comprises: providing a rear seal gland in the plunger, axially spaced to the rear of the front seal gland and extending circumferentially around the plunger; providing a rear o-ring made of a diene rubber compound; positioning the rear o-ring in the rear seal gland; and creating a sliding gas-tight seal between the inner surface of the barrel and the plunger. In some embodiments, the method further comprises: defining a head with a front end of the plunger, the head including the contact surface, and an outer diameter of the head being slightly smaller than an inner diameter of the barrel such that the head fits within the barrel with close tolerances; forming in a rear end of the plunger an integrally-formed molded ring having a maximum outer diameter that is slightly less than an inner diameter of the barrel such that the integrally-formed molded ring fits within the barrel with close tolerances; and resisting tipping of the plunger within the barrel with the head and integrally-formed molded ring during movement of the plunger within the barrel. In some embodiments, the step of freezing the product-filled syringe includes freezing the product-filled syringe at a temperature of about −25° C. while maintaining the gas-tight seal; and wherein the step of thawing the frozen product-filled syringe includes thawing the product-filled syringe to temperatures of about 40° C. while maintaining the gas-tight seal. In some embodiments, providing a plunger includes molding the plunger as a single piece with a parting line in the front seal gland arising from the molding process; the method further comprising the step of surface treating the front o-ring with a lubricant to gas-tightly seal the front o-ring with respect to the parting line in the front seal gland. In some embodiments, providing a plunger includes separately molding a front portion of the plunger and a rear portion of the plunger; wherein molding the front portion includes using axially-engaging mold portions to form a portion of the front seal gland with no parting lines; wherein molding the rear portion includes using radially-engaging mold portions to form a portion of the front seal gland with parting lines; the step of providing a plunger further comprising snap-fitting the front portion of the plunger and rear portion of the plunger together to define the front seal gland; wherein the front seal gland includes no leak paths between the o-ring and the portion of the front seal gland provided by the front portion of the plunger.

The invention also provides a syringe for use in a drug infusion system, the syringe comprising: a barrel having a front end, a rear end, and a cylindrical wall defining an outer surface and an inner surface, the rear end being open, and the front end including an orifice; a plunger within the barrel, the plunger including a front end and defining an external seal surface; an overmolded seal constructed of one of a thermoplastic rubber and a thermoplastic elastomer covering the front end of the plunger and the external seal surface, the overmolded seal covering the front end of the plunger to define a contact surface over the front end of the plunger, and a radially-extending wiper that creates a gas-tight seal between the inner surface of the barrel and the plunger; wherein a product chamber is defined between the inner surface of the barrel, the radial wiper of the overmolded seal, and the contact surface; wherein the product chamber is adapted to contain a product to be dispensed by the syringe; wherein actuation of the plunger within the barrel decreases the volume of the product chamber to dispense the product through the orifice; and wherein the radial wiper is sized to maintain the gas tight seal through a temperature range of −25° C. to 40° C.

In some embodiments, the overmolded seal is molded over the front end of the plunger to ensure a gas-tight seal between the overmolded seal and the external seal surface of the plunger. In some embodiments, the plunger includes a rear circumferential seal gland axially spaced to the rear of the overmolded seal, the syringe further comprising: a rear o-ring made of a diene rubber compound; wherein the rear o-ring is positioned in the rear seal gland; and wherein the rear o-ring creates a gas-tight seal between the inner surface of the barrel and the plunger. In some embodiments, a rear end of the plunger includes an integrally-formed molded ring having a maximum outer diameter that is slightly less than an inner diameter of the barrel such that the integrally-formed molded ring fits within the barrel with close tolerances; and wherein the radially-extending wiper and the integrally-formed molded ring resist tipping of the plunger within the barrel. In some embodiments, the radial wiper is sized to maintain the gas tight seal through a temperature range of −20° C. to 40° C. In some embodiments, the radial wiper is a front radial wiper, the overmolded seal further including a rear radial wiper spaced axially from the front radial wiper; wherein the rear radially-extending wiper creates a gas-tight seal between the inner surface of the barrel and the plunger.

In some embodiments, the syringe further comprises a deflectable tab in the plunger and an insert that deflects the deflectable tab radially outwardly; wherein the deflectable tab, when deflected outwardly by the insert, bears against the inner surface of the barrel to prevent tipping of the plunger in the barrel. In some embodiments, the deflectable tab includes a plurality of deflectable tabs; and wherein the insert includes a ring-shaped insert the expands all deflectable tabs radially outwardly. In some embodiments, the plunger further includes a second flexible wiper that is not part of the overmolded seal, the second flexible wiper engaging the inner surface of the barrel to prevent tipping of the plunger in the barrel. In some embodiments, the flexible wiper is integrally formed with the plunger. In some embodiments, the plunger further includes a circumferential slot; and wherein the wiper is inserted into the circumferential slot and extends radially outwardly into contact with the barrel inner surface.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
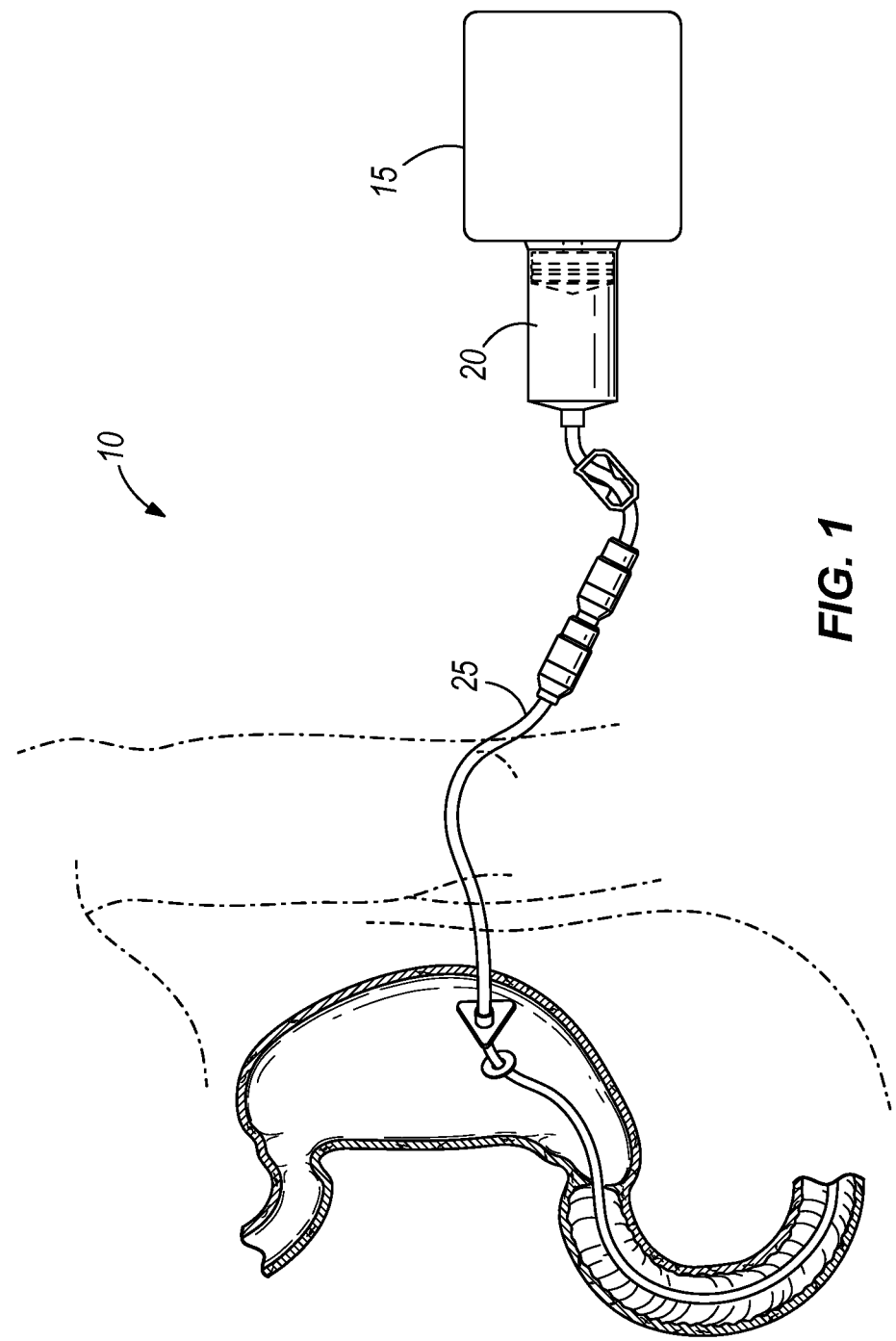
FIG. 1 illustrates an exemplary drug infusion system in which the present invention may be used.

FIG. 1 illustrates a drug infusion system 10 that includes a pump 15, a syringe 20, and a delivery tube 25 that can be inserted into a patient's small intestine. The pump 15 actuates the syringe 20, which displaces product from the syringe 20 into the patient through the tube 25. In many drug infusion systems, the pump actuates the syringe in a slow, steady manner, such that the patient receives the product at an optimal rate over an extended period. The pump can be programmed to deliver the product at a desired rate or according to a desired profile, and the program can be modified in response to the patient's reaction to the product.

An example of a pump that is currently used for drug infusion systems is the Canè Crono pump. Information regarding the Cane Crono pump is available at the company's website microjet.it. The Cane Crono pump is cited as merely one example of a pump which can be used in a drug infusion system as contemplated by the present invention. The findings and learnings of the present invention can be applied to drug infusion systems utilizing other pumps; the present invention should not be limited to the specific system illustrated or described. Indeed, the invention involves advances in syringe design (and, more specifically, the design of the plunger and sealing arrangements in the syringe) and should not be viewed as limited to the application of a drug infusion system. A drug infusion system is one environment in which such syringe design may be used and is provided here as an example only.

One example of a product administered through a drug infusion system is the Levodopa Carbidopa Intestinal Gel (LCIG) sold under the trademark DUODOPA by Abbott Laboratories. LCIG is used for treating patients with Advanced Parkinson's Disease. As the name implies, LCIG is a gel. The gel is about ninety-six percent (96%) water and therefore behaves much as water behaves during phase changes. Other formulations of LCIG may include a water content of about 94-95%, about 94.58%, or a water content of at least 84%.

LCIG is typically filled into a syringe post-manufacture, and the syringe and its contents are frozen and stored. Depending on its specific composition, the LCIG may have a freezing temperature of about −2° C. (28.4° F.). To ensure the LCIG is solidly frozen, it may be exposed to and stored at temperatures well below the freezing point. The syringes for LCIG product must be gas tight during a two-year storage period and during any shipping of the product. The storage and shipping environment may be maintained, for example, at about negative twenty degrees Celsius (−20° C.) (−4° F.) to ensure the product is solidly frozen.

Materials of construction should be compatible with LCIG during shelf life. The syringe should withstand stress during shipping.

The LCIG must be free from leak paths (i.e., it must be gas tight) during storage, shipping, thawing, and administering. Thawing may be done in a refrigerator at about two degrees Celsius to eight degrees Celsius (2 to 8° C.) (35.6° F. to 46.4° F.), for example, prior to being administered to a patient through the drug infusion system. To meet the expected freezing, shipping, thawing, and administering environments, the syringes should accommodate any temperatures and ranges of temperatures between negative twenty-five and forty degrees Celsius (−25° C. to 40° C.) (−13° F. to 104° F.) while maintaining seal integrity (i.e., a gas-tight seal that is free from leak paths). Within this range, the syringes should remain gas tight during a phase change of the gel from liquid to solid and from solid to liquid, which may occur, for example, around −2° C. (28.4° F.). Expected temperature ranges for the syringes include −20° C. to 2° C. (−4° F. to 35.6° F.), −20° C. to 8° C. (−4° F. to 46.4° F.), −20° C. to 40° C. (−4° F. to 104° F.), and −25° C. to 40° C. (−13° F. to 104° F.). The syringes should remain gas tight without regard to the rate of thawing.

Because of the high water content, the product expands as it freezes, and contracts as it thaws. When a filled syringe is placed at −20° C., the gel expands about nine percent (~9%) primarily in the axial direction & pushes the plunger outwards. The stability of the product can be compromised upon mixing with air, the addition of air to the gel may result in a decrease in delivery accuracy of the product to the patient, and there is no provision for the patient or care giver to remove air from the product prior to administration. Consequently, the syringe must accommodate expansion and contraction of the product without permitting air to permeate through the various seals within the syringe.

During the freeze-thaw cycle of a syringe with a conventional, known plunger sealing arrangement, it was observed that: there is a difference in thermal contraction between thermoplastic material, such as polypropylene, and rubber components; there are inadequate dimensions to provide sufficient sealing between the plunger and the syringe barrel over a wide temperature range (−25 to 40° C.); and the plunger can tilt/cock/rack during freezing or thawing reducing seal integrity. The result of these conditions leads to ingression of air into the gel during the thaw cycle.

Figure 2:
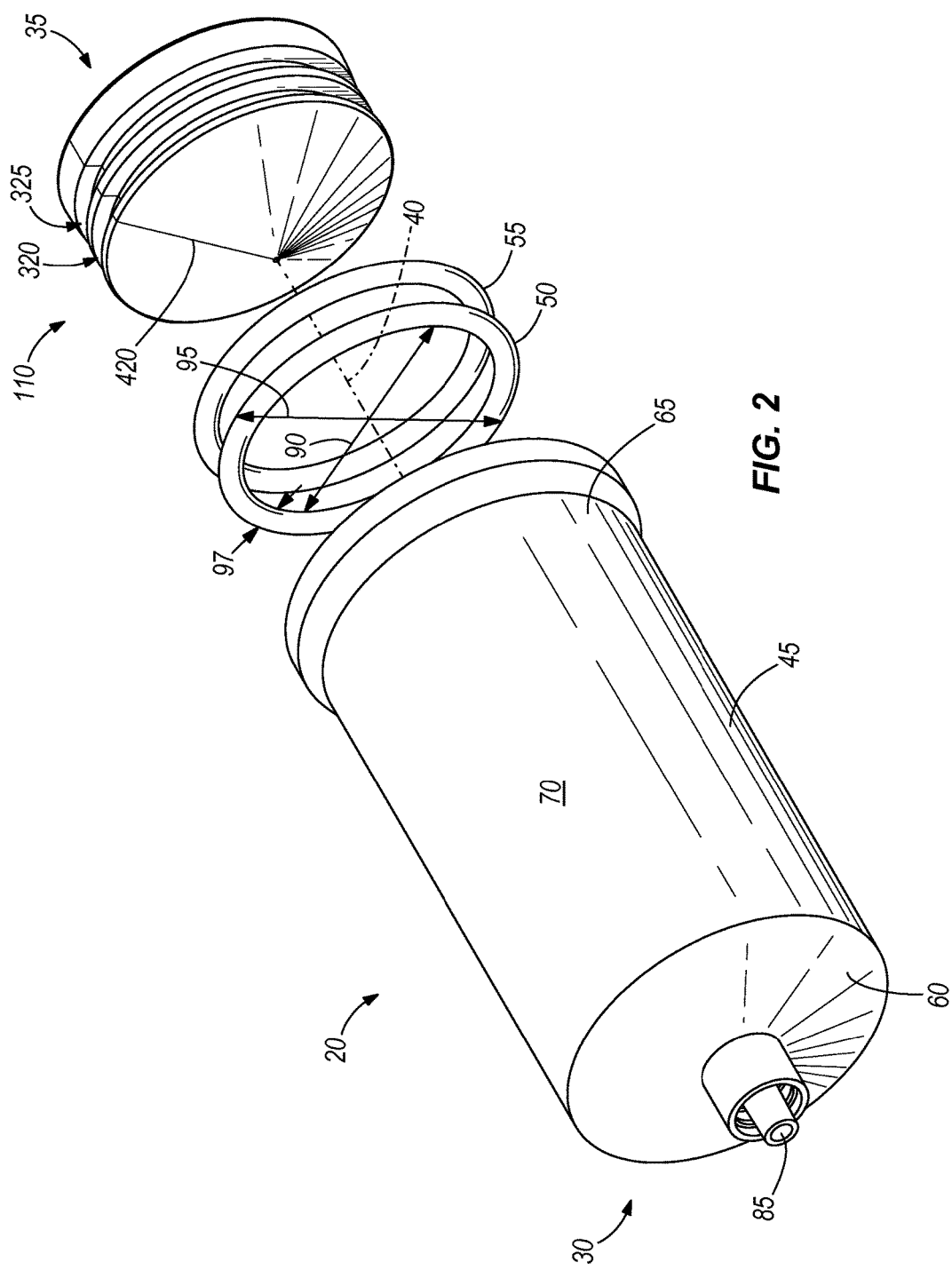
FIG. 2 is an exploded view of a syringe for use in the system illustrated in FIG. 1, the syringe including a barrel, a pair of o-rings, and a single-piece plunger according to a first embodiment of the invention.

With reference to FIG. 2, the syringe 20 includes a front end 30 and a rear end 35 and defines a longitudinal axis 40 extending between the front and rear ends 30, 35. Throughout this specification, the terms "front" and "forward" refer to portions, elements, and directions close to or in the direction of the front end 30 of the syringe 20, and the terms "rear" and "rearward" refer to portions, elements, and directions close to or in the direction of the rear end 35 of the syringe 20. The terms "axial" and "axially" mean in a direction parallel to the longitudinal axis 40 of the syringe 20, and the terms "radial" and "radially" mean in a direction perpendicular to the longitudinal axis 40.

Figure 4:
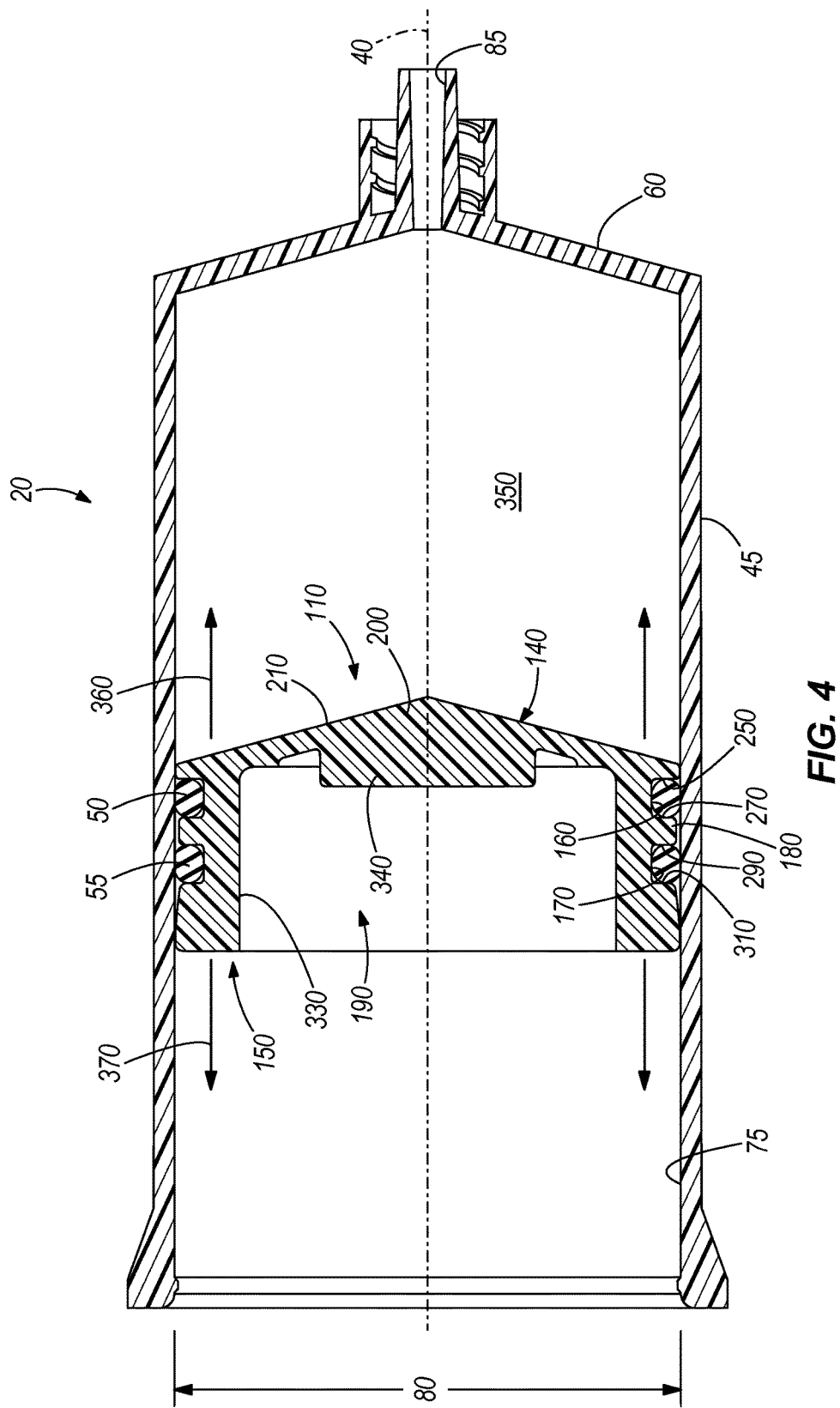
FIG. 4 is a cross-section view of the syringe including the single-piece plunger according to the first embodiment.

The syringe 20 includes a barrel 45, a front o-ring 50, a rear o-ring 55, and a plunger 110 (which may also be referred to as a piston). The barrel 45 is made of thermoplastic material, such as polypropylene, and includes a front end 60 and a rear end 65. The barrel 45 is generally cylindrical, having an outer surface 70 and an inner surface 75 (FIG. 4). The inner surface 75 of the barrel 45 defines a barrel diameter 80 (FIG. 4). An orifice 85 is formed in the front end 60. The orifice 85 communicates with the tube 25. The barrel 45 may include a flange for mounting the barrel 45 in the pump 15.

With reference again to FIG. 2, the front and rear o-rings 50, 55 are substantially identical. Each has an inner diameter (or "ID") 90, an outer diameter (or "OD") 95, and a thickness 97. The cross-sectional shape of the o-rings 50, 55 is circular, and the term "thickness" refers to the diameter of the cross-sectional shape of the o-ring when it is undeflected and at rest.

The o-rings 50, 55 are constructed of an appropriate formulation of diene rubber. As used herein, the phrase "diene rubber" includes butyl rubber, halogenated butyl rubber (such as chlorobutyl rubber and bromobutyl rubber), polybutadiene rubber, styrene-butadiene copolymer, synthetic polyisoprene, natural polyisoprene, styrene-isoprene copolymer, styrene-isoprene-butadiene terpolymer, solution-polymerized styrene-butadiene rubber, and emulsion-polymerized styrene-butadiene rubber, ethylene-propylene-diene rubber or combinations thereof. Although any diene rubber compound may be employed, two particularly suitable diene rubber compounds for use in pharmaceutical applications are chlorobutyl rubber and bromobutyl rubber, either of which may be used in the present invention. Bromobutyl or chlorobutyl rubber o-rings have significantly lower gas permeability (about 400× lower) than silicone.

Silicone rubber is an appropriate material o-rings in gas-tight seal applications in which there are no large pressure gradients across the seal. A potential example of an appropriate application for a silicone o-ring seal would be an environment in which the syringe and its contents are not frozen and then thawed. The present application involves a potentially large pressure gradient arising from vacuum developing within the LCIG during thawing, as will be discussed in detail below. As a result, silicone rubber would provide inadequate gas impermeability for the present application.

The phrases "gas tight," "gas-tightly," and variations of these phrases, when used in reference to a seal in the present disclosure, refer to the seal precluding the movement of air or other gases from one side of the seal to the other side of the seal in the presence of pressure gradients across the seal of a magnitude experienced during thawing of the product within the syringe as discussed herein, which may in some scenarios be on the order of one atmosphere (1 atm), for example.

The o-rings 50, 55 are surface treated with a lubricant. One suitable lubricant is silicone oil.

Figure 3:
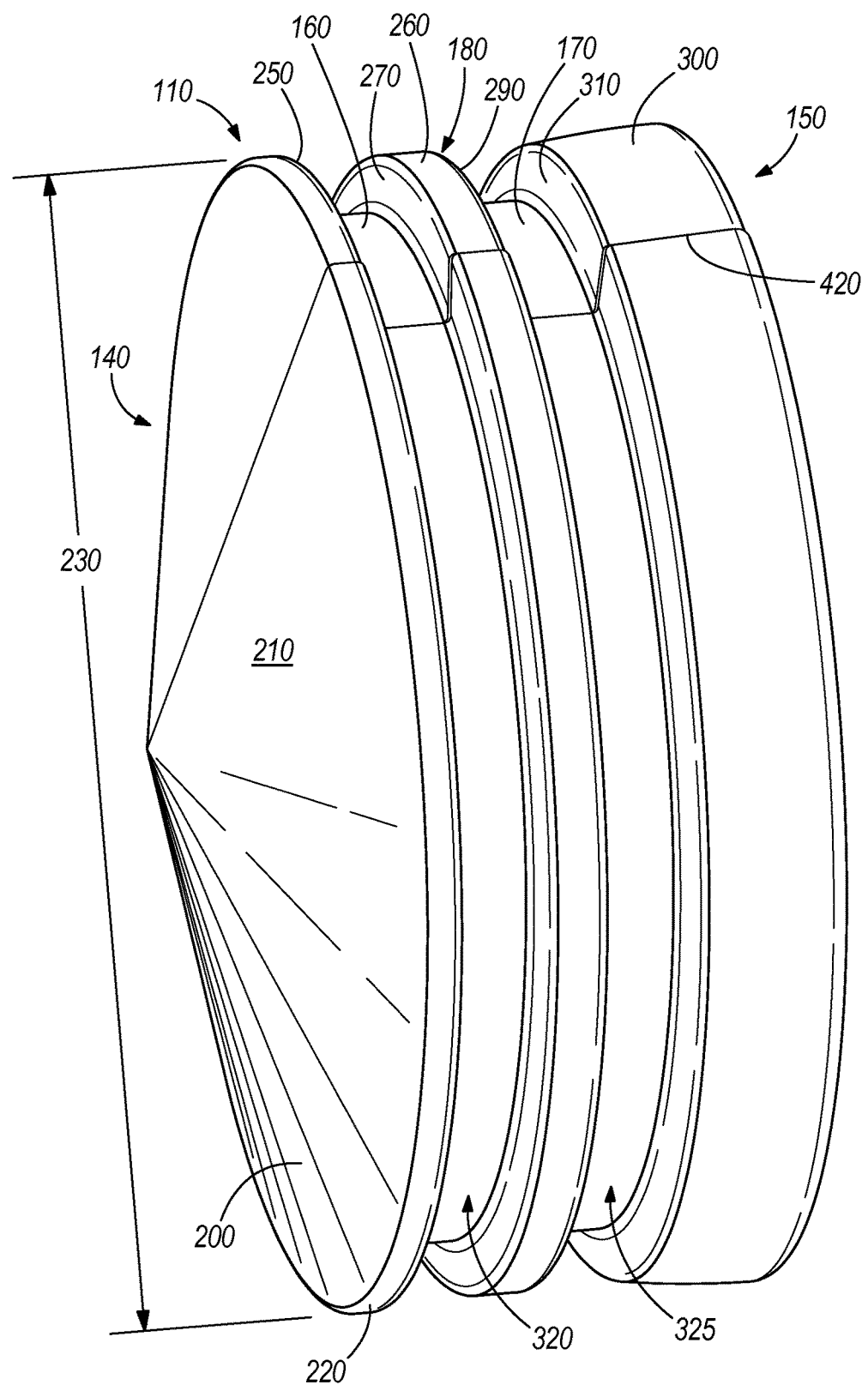
FIG. 3 is an enlarged perspective view of the single-piece plunger according to the first embodiment.

With reference to FIG. 3, the plunger 110 is also constructed of thermoplastic material, such as polypropylene, and includes a front end 140, a rear end 150, a front seal surface 160, a rear seal surface 170, a divider 180 between the front and rear seal surfaces 160, 170, and a blind bore 190 (FIG. 4). The front end 140 defines a head 200 that includes a contact surface 210 that extends from the center of the front end 140 to an outer edge 220 of the head 200. The contact surface 210 faces and contacts the product within the barrel 45. The contact surface 210 takes the form of a wide cone, and is the same shape as the front end 60 of the barrel 45 so that the contact surface 210 can nest with close tolerances within the front end 60 of the barrel 45 to push as much product out of the barrel 45 as possible. The outer diameter 230 of the head 200 (i.e., the diameter outer edge 220 of the head 200) is slightly less than the barrel diameter 80 such that the head 200 fits with close tolerances within the barrel 45, with the outer edge 220 of the head even brushing against the inner surface 75 of the barrel 45. The term "slightly less" is intended to mean that the outer diameter 200 of the head 230 (and, as will be discussed below, the wide end of the molded ring at the rear end 150 of the piston 110) is slightly smaller than an inner diameter 80 of the barrel 45 such that the head 230 and barrel 45 (and the molded ring and the barrel 45) can glide along each other, but the gap between them is small enough to prevent tipping of the plunger off axis to a degree that would negatively affect the sealing functionality of the o-rings 50, 55. In one exemplary embodiment, the gap between the barrel 45 and the head 230 (and molded ring) is about 0.002 inches.

The outer diameter 230 of the head 200 is wider than the diameter of the front seal surface 160, such that the head 200 defines a first rear-facing undercut 250 between the outer edge 220 of the head 200 and the front seal surface 160.

The divider 180 defines an outer surface 260 that is of smaller diameter than the outer diameter 230 of the head 200 (and therefore also of smaller diameter than the inner diameter 80 of the barrel 45). The divider 180 defines a first forward-facing undercut 270 between the outer surface 260 of the divider 180 and the front seal surface 160, and a second rear-facing undercut 290 between the outer surface 260 of the divider 180 and the rear seal surface 170.

The rear end 150 of the plunger 110 defines a tapered outer surface 300. The rear end 150 defines a second forward-facing undercut 310 between the tapered outer surface 300 and the rear seal surface 170. The rear seal surface 170 has an outer diameter equal to the outer diameter of the front seal surface 160. The tapered outer surface 300 increases in diameter from the second forward-facing undercut 310 to the rear end 150 of the plunger 110. The diameter of the tapered outer surface 300 is less than the barrel diameter 80 at the second forward-facing undercut 310, and reaches a diameter equal to the outer diameter 230 of the head 200 (i.e., slightly less than the barrel diameter 80) at the rear end 150 of the plunger 110.

The rear end 150 of the plunger 110 is therefore in close proximity to and may even brush against the inner surface 75 of the barrel 45. The rear end 150 of the plunger 110 may be referred to as a molded ring that is integrally formed with the plunger 110. Because the molded ring has a close dimensional fit within the barrel 45, the molded ring will prevent the plunger 110 from tipping about an axis that is perpendicular to the longitudinal axis 40 (such tipping sometimes referred to as "racking"). When the plunger 110 racks, the respective centerlines of plunger 110 and barrel 45 are not collinear. As the rack angle increases, the contact region for the o-rings 50, 55 shifts from circular to elliptical. The minor axis of the ellipse is the barrel inner diameter 80, and the major axis is the inner diameter divided by the cosine of the racking angle. The larger sealing diameter results in reduced interference and contact pressure between the o-rings 50, 55 and the barrel 45, which can compromise the gas-tight seal at the OD of the o-rings 50, 55.

The first rear-facing undercut 250, front seal surface 160, and first forward-facing undercut 270 may together be referred to as the "front seal seat" or the "front seal gland," which extends circumferentially around the plunger 110. The combination of the rear-facing undercut 250, front seal 160, and first forward-facing undercut 270 will be referred to hereafter as the front seal gland 320. The second rear-facing undercut 290, rear seal surface 170, and second forward-facing undercut 310 may together be referred to as the "rear seal seat" or the "rear seal gland," which extends circumferentially around the plunger 110 and is axially spaced rearwardly from the front seal gland 320. The combination of the second rear-facing undercut 290, rear seal surface 170, and second forward-facing undercut 310 will be referred to hereafter as the rear seal gland 325.

Turning now to FIG. 4, the blind bore 190 of the plunger 110 is open at the rear end 150 of the plunger 110 and closed at the front end 140. The blind bore 190 includes a cylindrical portion 330, and a plunger seat 340, which is on the rear-facing side of the head 200 of the plunger 110.

The syringe 20 is assembled by seating the front o-ring 50 in the front seal gland 320 and seating the rear o-ring 55 in the rear seal gland 325. The at-rest, pre-installation inner diameter 90 of each o-ring 50, 55 is smaller than the outer diameter of the front and rear seal surfaces 160, 170 to give rise to significant interference with the plunger 110 when the o-rings 50, 55 are installed. The at-rest, pre-installation outer diameter 95 of each o-ring 50, 55 is slightly smaller (e.g., about 0.3 mm) than the inner diameter 80 of the barrel 45, but when installed on the plunger 110 the outer diameter 95 expands to a diameter that is larger than the inner diameter 80 of the barrel 45 to seal against the inner surface 75 with a sufficient contact pressure to maintain a gas tight seal over an expected temperature range.

The plunger 110 is then inserted into the rear end 65 of the barrel 45. The o-rings 50, 55 deflect or compress between the plunger 110 and the inner surface 75 of the barrel 45 such that the o-rings 50, 55 seal at their outer diameters to the inner surface of the barrel 45 and at their inner diameters to the front and rear seal glands 320, 325.

The deflection or compression of the o-rings 50, 55 gives rise to a contact pressure between the o-rings and the barrel 45 and plunger 110. In practice, contact pressure is partially a function of the relative diameters of the barrel 45 and plunger 110. Molded parts, such as the barrel 45 and plunger 110 are made with a plus-minus tolerance. If the barrel 45 inner diameter is on the high end of its tolerance while the plunger 110 outer diameter is on the low end of its tolerance, a relatively loose fit can result. If the components are at the opposite ends of their tolerances (i.e., small inner diameter of barrel 45 and large outer diameter of plunger 110), a relatively tight fit can result. The compression of the o-rings 50, 55, and resultant contact pressure, is relatively low in a loose fit and relatively high in a tight fight. The o-rings 50, 55 are designed to maintain a gas tight fit between the barrel 45 and plunger 110 in the expected range of loose fit to tight fit based on the tolerances of the molded components. The o-rings 50, 55 are also designed to maintain the gas tight fit in the expected temperature range of −25° C.-40° C. for loose and tight fitting components.

For o-rings 50, 55 constructed of the diene rubber compounds contemplated by the present invention, the contact pressure range to accommodate tolerances and temperature ranges while maintaining a gas-tight seal between the barrel 45 and the plunger 110 is in the range of 40-120 psi. The inventors expect that the same contact pressure ranges will apply to all sealing members in all embodiments of the invention, including the o-rings and the TPE overmolded wipers of the embodiments discussed below. Another factor in designing for the appropriate contact pressure is the hardness of the material forming the seal. Depending on the type of material, contact pressure to maintain gas-tight sealing in the range of temperatures may vary from 20 psi to 400 psi.

The o-rings 50, 55 therefore create a sliding gas-tight seal between the plunger 110 and the barrel 45. A product chamber 350 is defined by the inner surface 75 of the barrel 45, the front o-ring 50, and the contact surface 210. When the plunger 110 is at rest in the barrel 45, the frictional force between the barrel inner surface 75 and the front and rear o-rings 50, 55 may be referred to as the static friction of the plunger 110. In the presence of a force that overcomes the static friction of the plunger 110, the plunger 110 is moved axially within the barrel 45 in a forward direction 360 and a rearward direction 370 to decrease and increase, respectively, the volume of the product chamber 350.

Initially, the plunger 110 is pushed to the full-forward position in which the contact surface 210 abuts the inner surface 75 of the barrel 45 at the front end 60, and the volume of the product chamber 350 is essentially zero. Product is forced into the syringe 20 through the orifice 85 under pressure sufficient to overcome the static friction of the plunger 110. This forces the plunger 110 to move rearwardly, which expands the product volume. Once a desired product volume is reached, the product-filled syringe 20 is frozen.

In the case of LCIG, or another product having a high water content, freezing the product-filled syringe 20 will cause the product to expand as the water freezes. Expansion of the product-filled syringe 20 will overcome the static friction of the plunger 110 and force the plunger 110 rearwardly 370, which also expands the volume of the product chamber 350. Expansion of the product may also cause hoop stress in the barrel 45, which radially expands the inner diameter 80 of the barrel 45. The product will take the path of least resistance when expanding, however, so if the static friction of the plunger 110 is low enough, there will be minimal radial or circumferential expansion of the barrel 45 because the product will expand primarily in the axial direction.

The barrel 45 and plunger 110 are made of the same material and will therefore exhibit similar thermal expansion and contraction, such that the gap between the barrel 45 and plunger 110 will not materially change during thermal cycling. The o-rings 50, 55 will contract as they are frozen, resulting in a lowering of the static friction of the plunger 110 as temperature drops. The dimensions of the front and rear o-rings 50, 55 (i.e., inner diameter, outer diameter, and thickness) are selected to accommodate shrinkage of the o-rings 50, 55 and expansion of the barrel inner diameter 80 while maintaining the sliding gas-tight seal between the plunger 110 and the barrel 45 and at the same time minimizing static friction of the plunger 110.

The syringe 20 and product will thaw radially inwardly from the outer diameter of the barrel 45. As a consequence, the product will contain an axially-extending column of ice that shrinks in diameter as the product thaws. The column of ice extends from the front end 60 of the barrel to the contact surface 210 of the plunger 110. The column of ice resists movement of the plunger 110 in the forward direction 360, which therefore resists or slows down the shrinking of the volume of the product chamber 350 during thawing. The portion of the product that thaws first (i.e., the radial periphery of the product) will contract faster than the volume of the product chamber 350 shrinks, which will give rise to pockets or bubbles of vacuum within the thawed portion of the product.

Because the vacuum arises on the radial periphery of the product, it is essentially directly forward of the front and rear o-rings 50, 55, which exposes the front and rear o-rings 50, 55 (especially the front o-ring) to the vacuum. The o-rings 50, 55 must provide sufficient resistance to gas permeability to maintain a gas-tight seal between the plunger 110 and the barrel 45 in the face of such vacuum so that air does not mix with the product during thawing. As the ice column melts, and provided that the vacuum force (i.e., the force arising from the vacuum pressure applied to the contact surface 210) overcomes the static friction of the plunger 110, the plunger 110 will be drawn forward 360 to shrink the product chamber 350 to the volume of the thawed product.

Once thawed, the syringe 20 is installed in the pump 15. The pump 15 includes a pushrod or other actuation element that is received within the blind bore 190 of the plunger 110. The pushrod may be secured within the blind bore 190 to the seat 340 by, for example, a slip fit, interference fit, or threaded fit. The pump 15 applies a linear force on the plunger 110 through the pushrod to linearly displace the plunger 110 in the forward direction 360 within the barrel 45 along the longitudinal axis 40. As the plunger 110 moves in the forward direction 360, the volume of the product chamber 350 decreases and product is forced out the orifice 85, through the tube 25, and into the patient at a rate prescribed by the physician.

Figure 5:
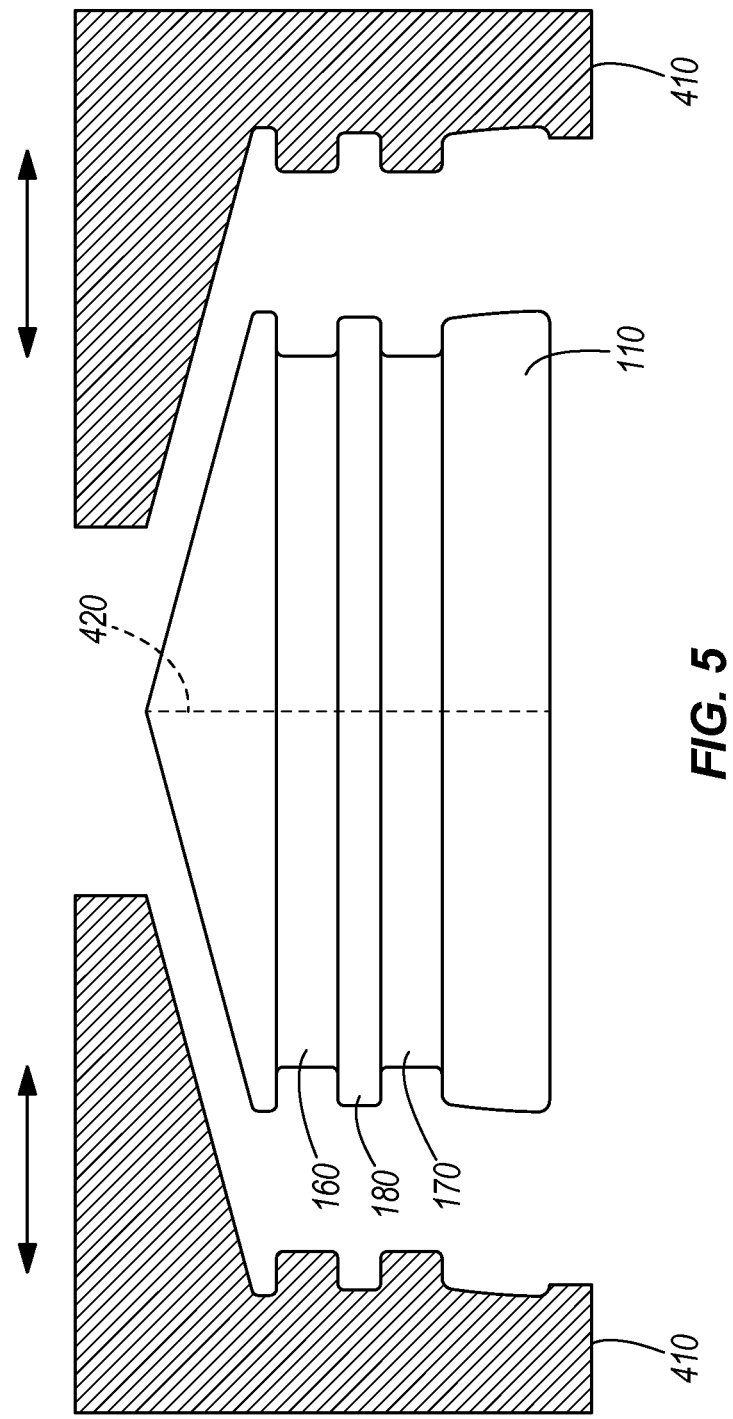
FIG. 5 is a schematic illustration of the molding process for the single-piece plunger according to the first embodiment.

FIG. 5 schematically illustrates a method of forming the single-piece plunger 110 described above. The illustration is greatly simplified for the purposes of this disclosure. The mold includes right and left halves or slides 410 that are inserted and removed radially, and a third mold portion (not shown) that is inserted and removed axially to form the blind bore 190. The right and left halves 410 must be inserted and removed radially to form the undercuts 250, 270, 290, 310. It can be expected in a production environment that there will be axial misalignment of the right and left halves 410, which will cause a parting line 420 to be formed in the plunger 110, and which will cause the left and right sides of the front and rear seal glands 320, 325 to have some misalignment. Such misalignment may take the form of a small step in the front and rear seal glands 320, 325.

Such misalignment is expected to be minor, even in a product environment, but the misalignment will give rise to a leak path at both parting lines. Due to their small size, the leak paths may be fluid tight but still leak air. In other words, the misalignment may give rise to gas permeation or a leak path on the ID of the o-rings 50, 55. Such misalignment is overcome with the lubricant (e.g., silicone oil) surface treatment of the o-rings 50, 55 prior to assembly, mentioned above. The lubricant fills any gaps that arise from the misalignment, and permits a gas-tight seal to be created and maintained between the o-rings 50, 55 and the plunger 110. Because such misalignment is expected to be very small, the lubricant will not create a significant weakness in the overall gas-tight seal created by the o-rings 50, 55.

Figure 6:
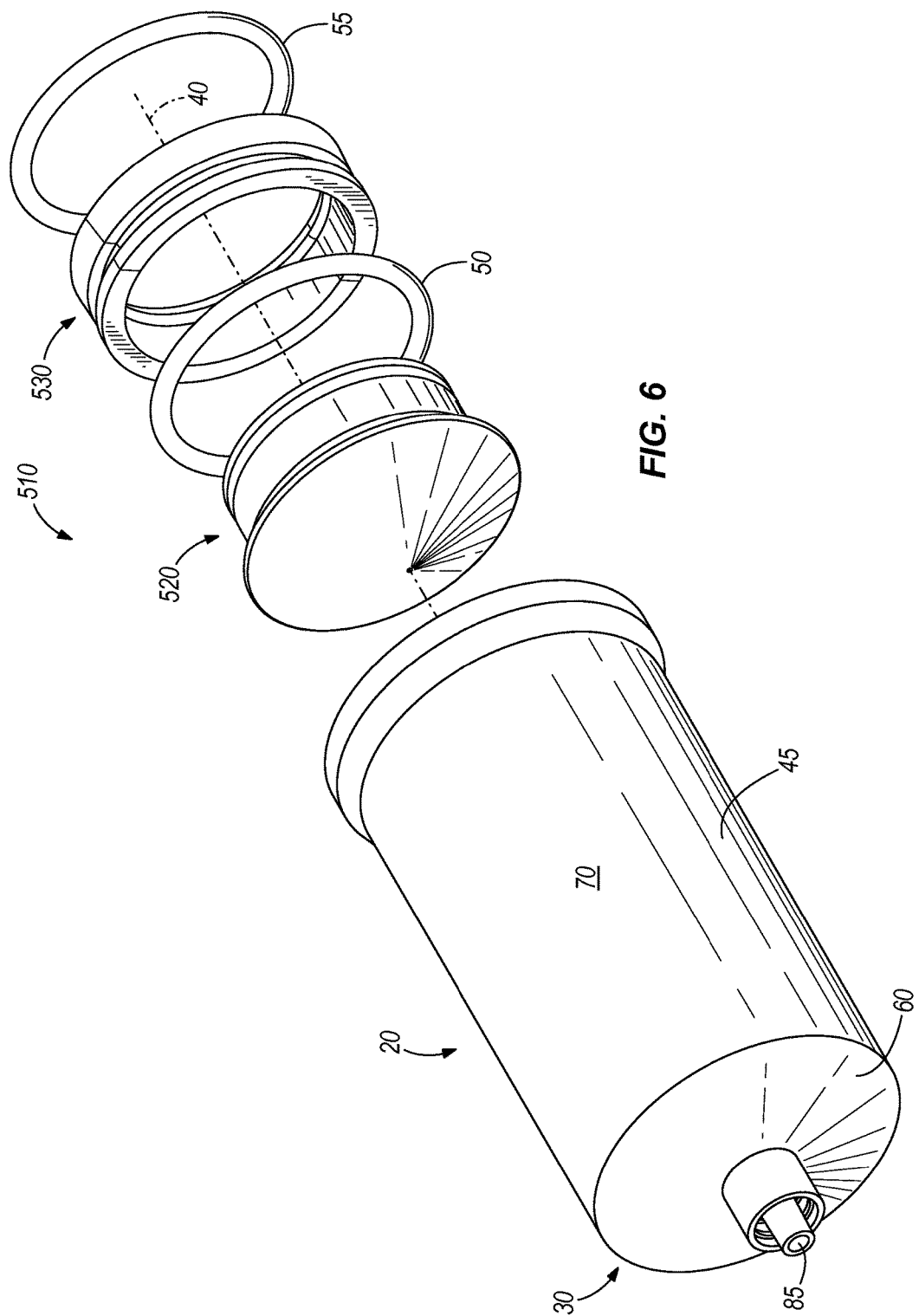
FIG. 6 is an exploded view of a syringe for use in the system illustrated in FIG. 1, the syringe including a barrel, a pair of o-rings, and a two-piece plunger according to a second embodiment of the invention.

A second embodiment of the plunger 510 will now be described with reference to FIGS. 6-11. As illustrated in FIG. 6, the syringe barrel 45 and front and rear o-rings 50, 55 are identical to the embodiment described above with respect to the single-piece version of the plunger 110. This embodiment includes a two-piece plunger 510 that comprises a front portion 520 and a rear portion 530, both of which are constructed of thermoplastic material, such as polypropylene.

Figure 7:
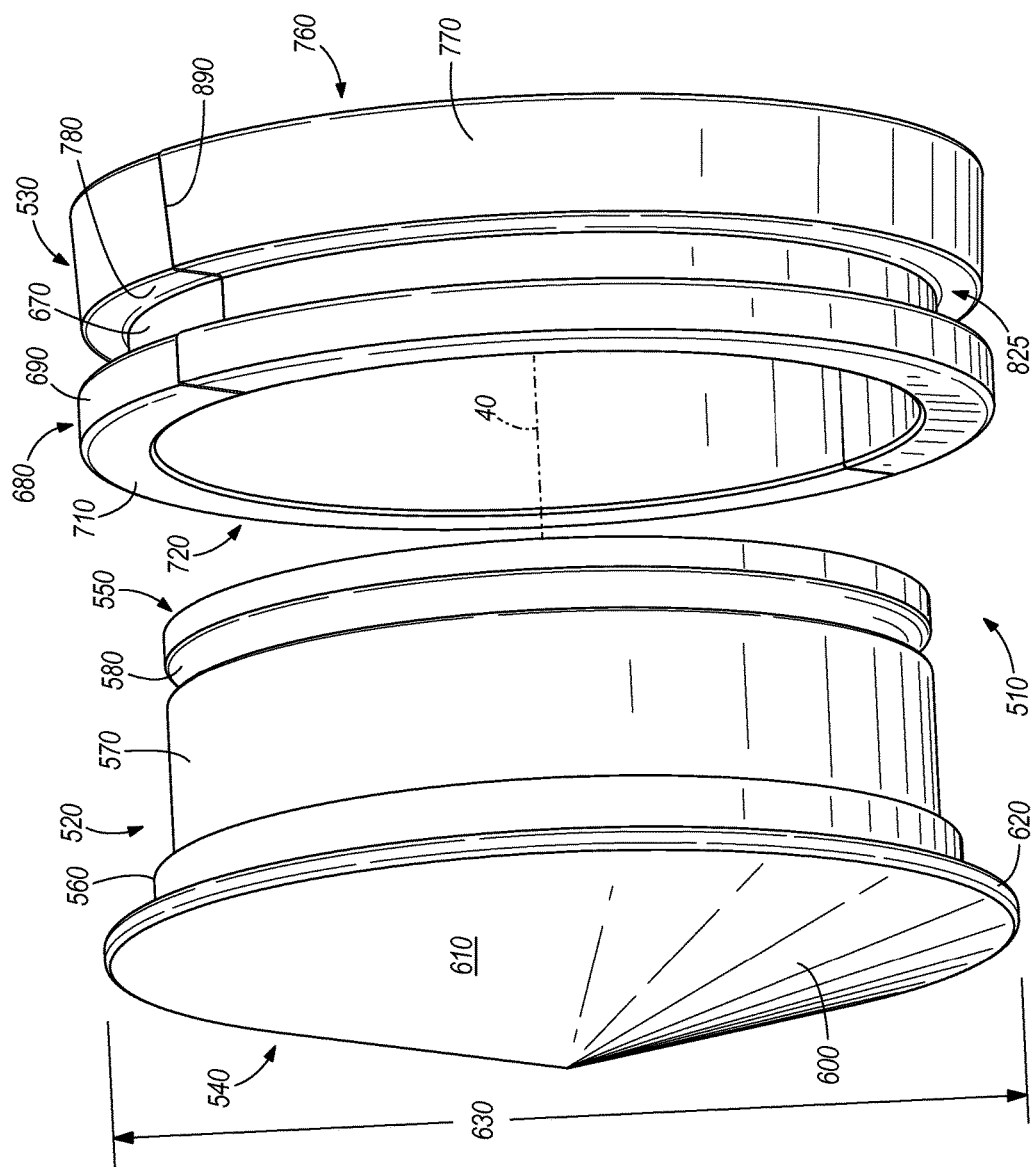
FIG. 7 is an enlarged exploded view of the two-piece plunger according to the second embodiment.
Figure 8:
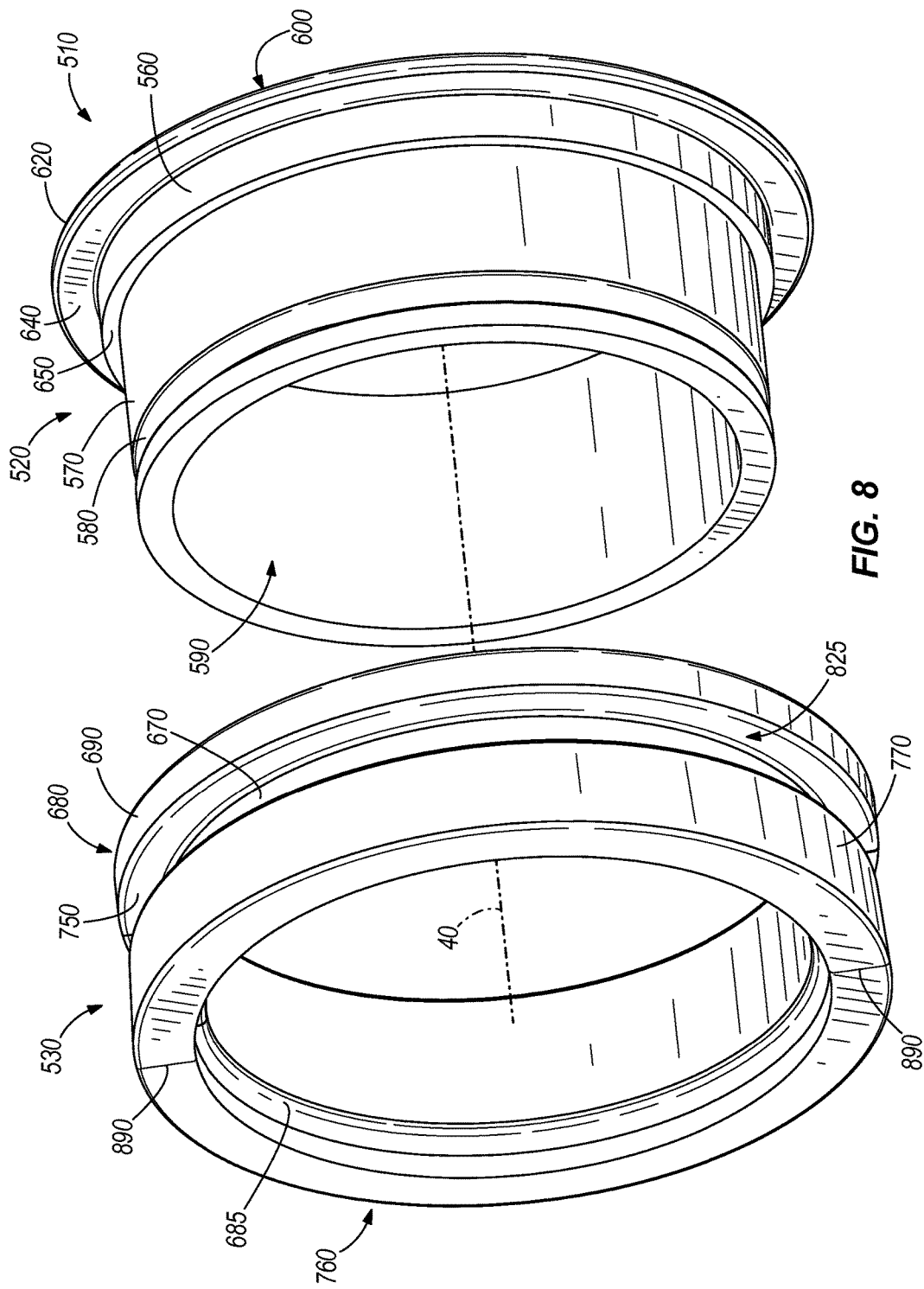
FIG. 8 is an enlarged exploded view of the two-piece plunger according to the second embodiment, taken from a perspective different from that of FIG. 7.

With reference to FIGS. 7 and 8, the front portion 520 includes a front end 540, a rear end 550, a front seal surface 560, a skirt 570, a detent groove 580, and a blind bore 590 (FIG. 8). The front end 540 defines a head 600 that includes a contact surface 610 that extends from the center of the front end 540 to an outer edge 620 of the head 600. The contact surface 610 faces and contacts the product within the barrel 45. The contact surface 610 takes the form of a wide cone, and is the same shape as the front end 60 of the barrel 45 so that the contact surface 610 can nest with close tolerances within the front end 60 of the barrel 45 to push as much product out of the barrel 45 as possible. An outer diameter 630 of the head 600 (i.e., the diameter outer edge 620 of the head 600) is slightly less (i.e., to reduce or eliminate racking) than the barrel diameter 80 such that the head 600 fits with close tolerances within the barrel 45, with the outer edge 620 of the head 600 even brushing against the inner surface 75 of the barrel 45. The outer diameter 630 of the head 600 is wider than the diameter of the front seal surface 560, such that the head 600 defines a first rear-facing undercut 640 between the outer edge 620 of the head 600 and the front seal surface 560.

The skirt 570 extends rearward of the front seal surface 560, is cylindrical, and has an outer diameter that is smaller than the outer diameter of the front seal surface 560. As a result, a shoulder 650 (FIG. 8) is formed where the outer diameter of the front portion 520 steps down from the front seal surface 560 to the skirt 570. The detent groove 580 is formed in the outer surface of the skirt 570 and extends unbroken around the entire circumference of the skirt 570.

The rear portion 530 is generally ring-shaped and includes a rear seal surface 670, a divider 680, and a detent ridge 685 (FIG. 8). The divider 680 defines an outer surface 690 that is of smaller diameter than the outer diameter 630 of the head 600 (and therefore also of smaller diameter than the inner diameter 80 of the barrel 45). The divider 680 defines a first forward-facing undercut surface 710 at a front end 720 of the rear portion 530, and a second rear-facing undercut 750 (FIG. 8) between the outer surface 690 of the divider 680 and the rear seal surface 670.

A rear end 760 of the rear portion 530 of the plunger 510 defines a tapered outer surface 770. The rear end 760 defines a second forward-facing undercut 780 between the tapered outer surface 770 and the rear seal surface 670. The rear seal surface 670 has an outer diameter equal to the outer diameter of the front seal surface 560. The tapered outer surface 770 increases in diameter from the second forward-facing undercut 780 to the rear end 760 of the rear portion 530 of the plunger 510. The diameter of the tapered outer surface 770 is less than the barrel diameter 80 at the second forward-facing undercut 780, and reaches a diameter equal to the outer diameter 630 of the head 600 (i.e., slightly less than the barrel diameter 80, for the purpose of preventing racking) at the rear end 760 of the rear portion 530 of the plunger 510.

The rear end 760 is therefore in close proximity to and may even brush against the inner surface 75 of the barrel 45. The rear end 760 may be referred to as a molded ring that is integrally formed with the rear portion 530. Because the molded ring has a close dimensional fit within the barrel 45, the molded ring will prevent the plunger 510 from tipping about an axis that is perpendicular to the longitudinal axis 40 (such tipping sometimes referred to as "racking"). When the plunger 510 racks, the respective centerlines of plunger 510 and barrel 45 are not collinear. As the rack angle increases, the contact region shifts from circular to elliptical. The minor axis of the ellipse is the barrel inner diameter, and the major axis is the inner diameter divided by the cosine of the racking angle. The larger sealing diameter results in reduced interference and contact pressure between the o-ring seals and the barrel, which can compromise the gas-tight seal at the OD of the o-rings.

The two-piece plunger is assembled by inserting the skirt 570 of the front portion 520 into the rear portion 530, and applying sufficient axial force to snap the detent ridge 685 into the detent groove 580. In other embodiments, the detent groove 580 and detent ridge 685 interconnection may be replaced with bead and recess detents, a threaded interconnection between the front portion 520 and rear portion 530, or any other suitable joining method.

Figure 9:
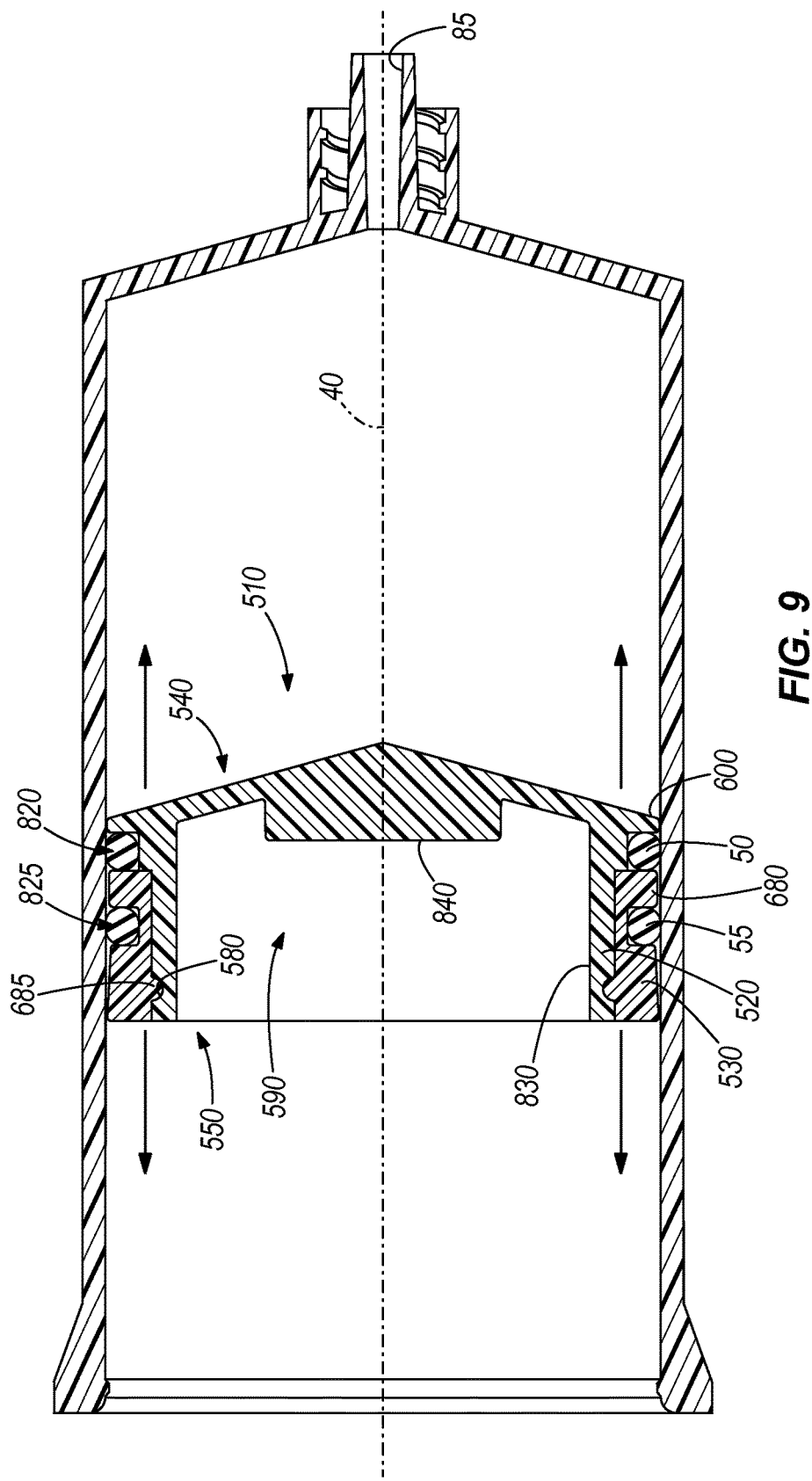
FIG. 9 is a cross-section view of the syringe including the two-piece plunger according to the second embodiment.

As assembled, the first rear-facing undercut 640, front seal surface 560, and first forward-facing undercut 710 may together be referred to as the "front seal seat" or the "front seal gland," which extends circumferentially around the plunger 510. The combination of the first rear-facing undercut 640, front seal surface 560, and first forward-facing undercut 710 will be referred to hereafter as the front seal gland 820 (FIG. 9). The second rear-facing undercut 750, rear seal surface 670, and the second forward-facing undercut 780 may together be referred to as the "rear seal seat" or the "rear seal gland," which extends circumferentially around the plunger 510 and is axially spaced rearwardly from the front gland 820. The combination of the second rear-facing undercut 750, rear seal surface 670, and the second forward-facing undercut 780 will be referred to hereafter as the rear seal gland 825 (FIG. 9).

Turning now to FIG. 9, the blind bore 590 of the plunger 510 is open at the rear end 550 of the plunger 510 and closed at the front end 540. The blind bore 590 includes a cylindrical portion 830, and a plunger seat 840, which is on the rear-facing side of the front end 540 of the plunger 510.

Figure 10:
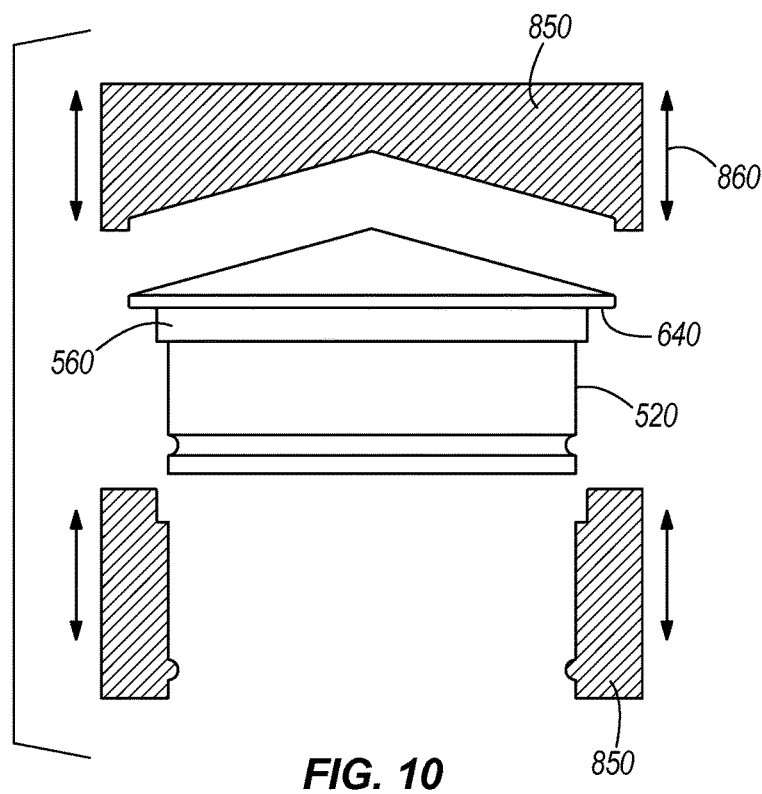
FIG. 10 is a schematic illustration of the molding process for the front portion of the two-piece plunger according to the second embodiment.

The molding arrangement for the front portion 520 of the two-piece plunger 510 is schematically illustrated in greatly simplified form in FIG. 10 (for example, there would be additional mold components to form the detent groove 580 and blind bore 590). This illustration is provided to show that the mold parts 850 for the front portion 520 move axially 860 rather than radially. As a result, there is no parting line across the first rear-facing undercut 640 or front seal surface 560, and the front o-ring 50 is able to gas-tightly seal within the front seal gland 820.

Figure 11:
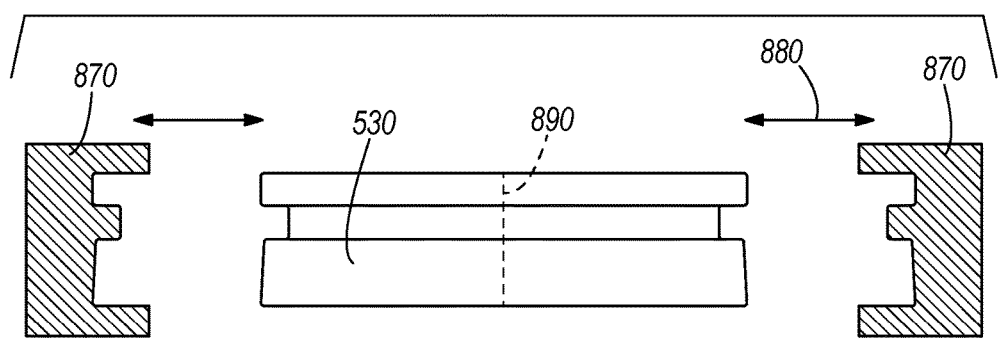
FIG. 11 is a schematic illustration of the molding process for the rear portion of the two-piece plunger according to the second embodiment.
Figure 12:
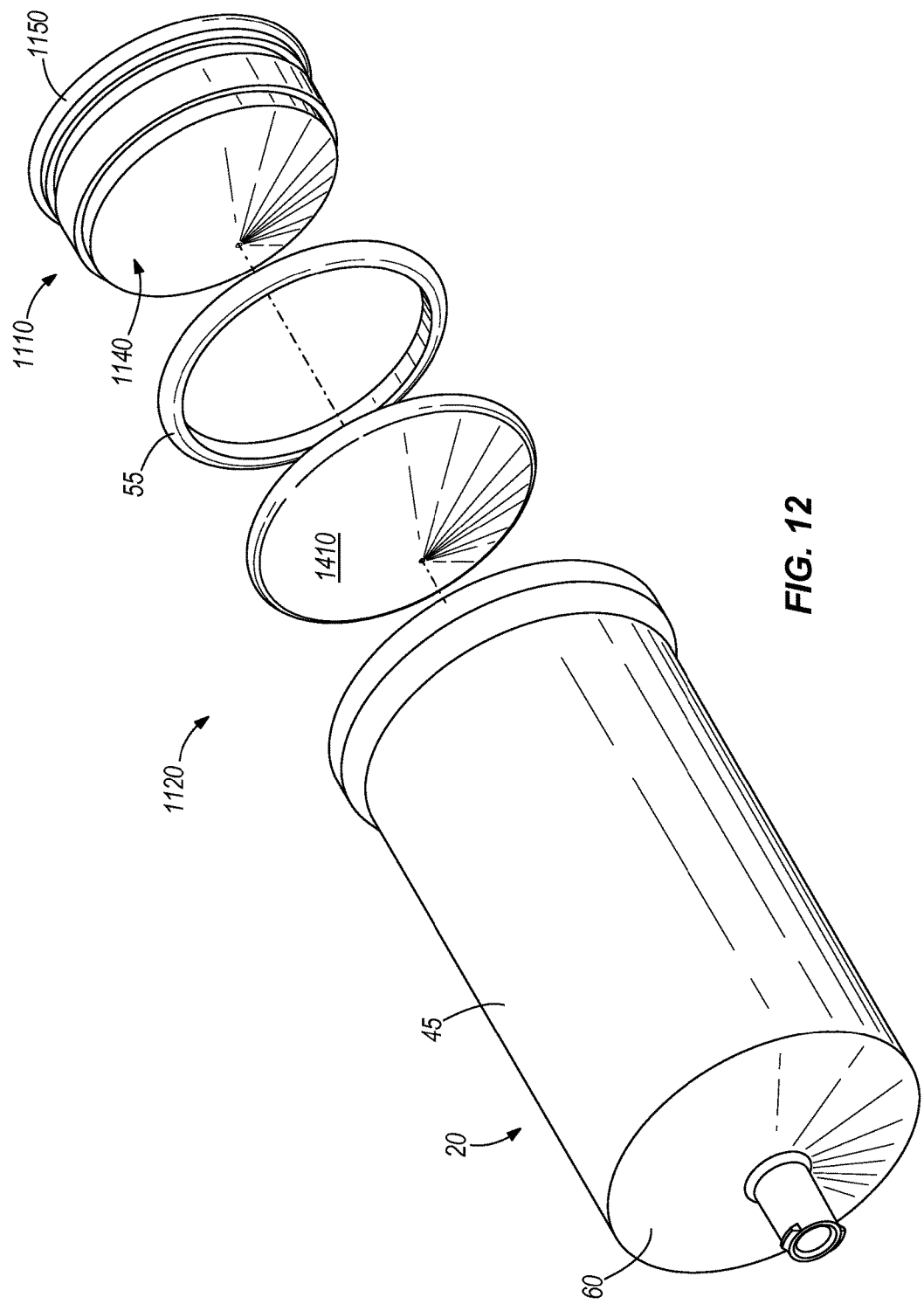
FIG. 12 is an exploded view of a syringe for use in the system illustrated in FIG. 1, the syringe including a barrel, an o-ring, an overmolded seal, and a plunger according to a third embodiment of the invention.

The rear portion 530 of the two-piece plunger 510 is molded with radially moving mold parts 870, as schematically illustrated in FIG. 11. Again, the illustrated molding process is greatly simplified to show the mold parts 870 move radially 880 (for example, there would be additional mold components for the inner cylindrical surface, detent ridge 685, and rear seal gland 825). This is because the integrity of the seal provided by the rear o-ring 55 is less important in this embodiment due to the superior sealing achieved by the front o-ring 50. Consequently, the two-piece plunger 510 embodiment can tolerate the parting line 890 and resulting small steps in the rear seal gland 825. As a factor of safety, the front and rear o-rings 50, 55 can be provided in this embodiment with a silicone surface treatment to improve the quality of the seals, as discussed above with respect to the single-piece plunger embodiment.

FIGS. 12-15 illustrate a first overmolded version of the plunger assembly, which is a third embodiment of the present invention. The first overmolded version includes a plunger 1110, an overmolded seal 1120, and the rear o-ring 55. The plunger 1110 is made of thermoplastic material such as polypropylene, the overmolded seal 1120 is made of thermoplastic elastomer (TPE), and the rear o-ring 55 is made of a diene rubber.

As used herein, the phrases "thermoplastic rubbers" and "thermoplastic elastomers" (collectively, for convenience thermoplastic rubbers and thermoplastic elastomers are referred to as "TPE") refer to a polymer blend or compound which, above its melt temperature, exhibits a thermoplastic character that enables it to be shaped into a fabricated article and which, within its design temperature range, possesses elastomeric behavior without cross-linking during fabrication. The process of making a TPE is reversible and the products can be reprocessed and remolded.

In order for a material to be considered to be a TPE, the material must exhibit the following three essential characteristics: (1) the ability to be stretched to moderate elongations and, upon the removal of stress, return to something close to its original shape (recovery); (2) processed as a melt at elevated temperature; and (3) absence of significant creep.

Even though TPEs are thermoplastic, they exhibit elasticity similar to that of a cross-linked rubber. A key indicator is their softness or hardness value as measured on the Shore durometer scale. Like crosslinked rubber, TPEs are available as very soft gel materials from 20 Shore OO up to 90 Shore A, at which point they enter the Shore D scale and can be formulated to give hardness values up to 85 Shore D, which designates a material that is very hard.

Generally, there are six generic classes of TPE's:

1) Styrenic Block Copolymers (TPE-S)— bSBS is based on two-phase block copolymers with hard and soft segments. The styrene end blocks provide the thermoplastic properties and the Butadiene mid-blocks provide the elastomeric properties. SBS when hydrogenated becomes SEBS, as the elimination of the C=C bonds in the butadiene component generated ethylene and butylenes midblock. SEBS is characterized by much improved heat resistance, mechanical properties and chemical resistance.

2) Thermoplastic Polyolefins (TPE-O or TPO)—

These materials are blends of polypropylene (PP) and un-crosslinked EPDM rubber, in some cases a low degree of cross-linking is present to boost heat resistance and compression set properties. They are used in applications where there is a requirement for increased toughness over the conventional PP copolymers. The properties are restricted to the high end of the hardness scale, typically >80 Shore A and with limited elastomeric properties.

3) Thermoplastic Vulcanisates (TPE-V or TPV)—

These materials are the next step up in performance from TPE-O. These are compounds of PP and EPDM rubber, however, they have been dynamically vulcanised during the compounding step. They exhibit heat resistance of up to 120° C. Shore hardness values range typically from 45A to 45D.

4) Thermoplastic Polyurethanes (TPE-U or TPU)—

These materials can be based on polyester or polyether urethane types and are used in applications where a product requires excellent tear strength, abrasion resistance, and flex fatigue resistance. Hardness is restricted to the high end of the Shore A scale, typically >80 Shore A.

5) Thermoplastic Copolyesters (TPE-E or COPE or TEEE)—

These materials are used where increased chemical resistance and heat resistance up to 140° C. are needed. They also exhibit good fatigue resistance and tear strength and so are used in automotive applications such as blow molded boots and bellows, wire and cable, and industrial hose applications. Again hardness is restricted to the high end and is typically between 85A to 75D.

6) Thermoplastic Polyether Block Amides (TPE-A)—

These products offer the good heat resistance, have good chemical resistance and bonding to polyamide engineering plastics.

It is believed that any of the materials listed in the above 6 classes would be useful for overmolded seals. It has been found though analysis that softer materials (such as those having 40-50 Durometer A) (e.g. TPE-S, TPE-V and some individual materials) can accommodate larger dimensional tolerances than harder materials (75-80 Durometer A). However, the stress relaxation rates may be higher in the softer materials, and so the seals may require additional interference or may be less durable than harder materials or crosslinked elastomers.

Figure 13:
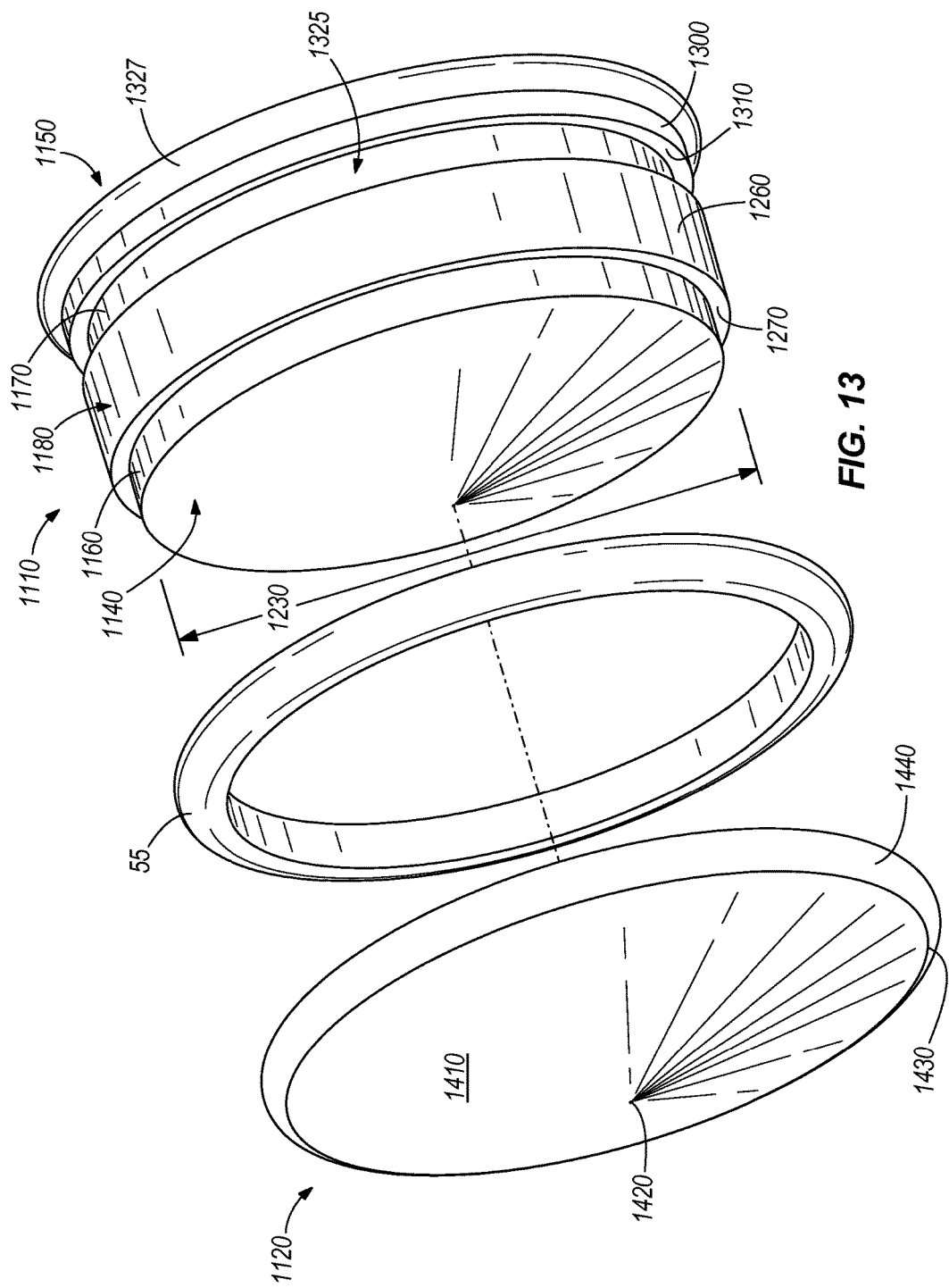
FIG. 13 is an enlarged perspective view of the plunger and seal assembly of FIG. 12.
Figure 14:
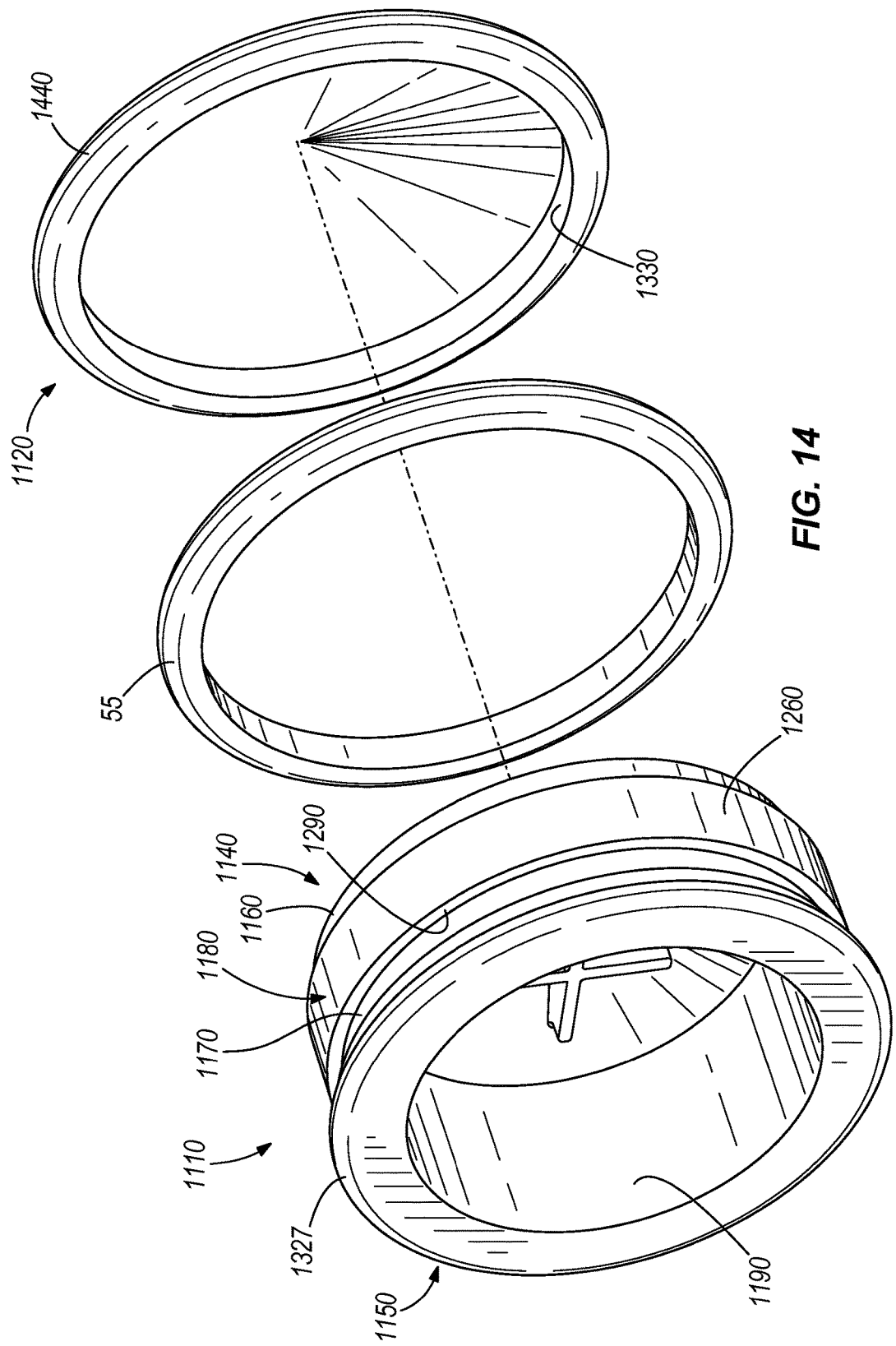
FIG. 14 is an enlarged perspective view of the plunger and seal assembly of FIG. 12 from a perspective different from FIG. 13.

Referring to FIGS. 13 and 14 in particular, the plunger 1110 includes a front end 1140, a rear end 1150, a front seal surface 1160, a rear seal surface 1170, a divider 1180 between the front and rear seal surfaces 1160, 1170, and a blind bore 1190 (FIG. 14). The front end 1140 takes the form of a wide cone, and is the same shape as the front end 60 of the barrel 45. The outer diameter 1230 of the front end 1140 is equal to the diameter of the front seal surface 1160, such that there is no radial step (outward or inward) at the transition from the front end 1140 to the front seal surface 1160.

The divider 1180 defines an outer surface 1260 that is of larger diameter than the front end 1140 but of smaller diameter than the inner diameter 80 of the barrel 45. The divider 1180 defines a first forward-facing undercut 1270 between the outer surface 1260 of the divider 1180 and the front seal surface 1160, and a rear-facing undercut 1290 between the outer surface 1260 of the divider 1180 and the rear seal surface 1170.

The rear end 1150 of the plunger 1110 defines a step-up in diameter from the rear seal surface 1170. The step-up includes an outer surface 1300 having a diameter equal to the outer surface 1260 of the divider 1180. The rear end 1150 defines a second forward-facing undercut 1310 between the outer surface 1300 and the rear seal surface 1170. The rear seal surface 1170 has an outer diameter equal to the outer diameter of the front seal surface 1160. The combination of the second rear-facing undercut 1290, rear seal surface 1170, and second forward-facing undercut 1310 may be referred to hereafter as the rear seal gland 1325. The rear seal gland 1325 extends circumferentially around the plunger 1110.

Rearward of the outer surface 1300, the rear end 1150 of the plunger 1110 includes a molded ring 1327 that is integrally formed with the plunger 1110. The molded ring 1327 is in close proximity to and may even brush against the inner surface 75 of the barrel 45. Because the molded ring 1327 has a close dimensional fit within the barrel 45, the molded ring 1327 will prevent the plunger 1110 from racking or reduce the degree of racking of the plunger 1110.

The overmolded seal 1120 is a single, integral piece that is molded over the front end 1140 and the front seal surface 1160 of the plunger 1110. Because the overmolded seal 1120 is molded over the front end 1140 and front seal surface 1160 of the plunger 1110, an inner surface 1330 of the overmolded seal 1120 exactly follows those portions of the plunger 1110. Molding the overmolded seal 1120 onto the plunger 1110 eliminates the inner leak path and improves sealing against the front seal surface 1160.

A front end of the overmolded seal 1120 defines a contact surface 1410 that extends from the center 1420 of the front end to an outer edge 1430 of the front end. The contact surface 1410 faces and contacts the product within the barrel 45. The contact surface 1410 takes the form of a wide cone, and is the same shape as the front end 60 of the barrel 45 so that the contact surface 1410 can nest with close tolerances within the front end 60 of the barrel 45 to push as much product out of the barrel 45 as possible.

A front radial wiper 1440 is molded as an integral part of the overmolded seal 1120. The front radial wiper 1440 extends radially from the outer edge 1430 of the front end of the overmolded seal 1120 and extends circumferentially around the plunger 1110.

Figure 15:
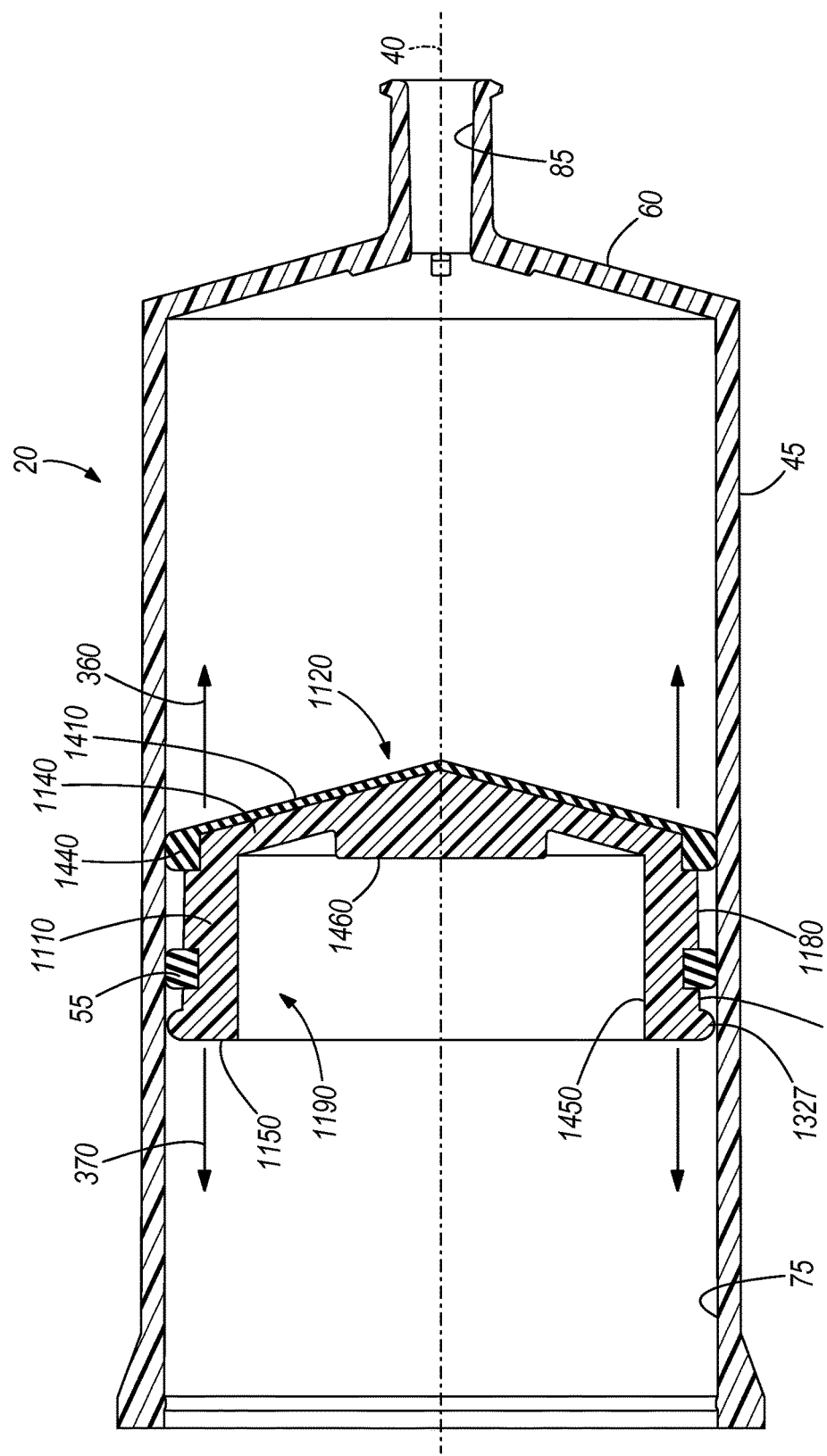
FIG. 15 is a cross-section view of the syringe including the plunger and seal assembly of FIG. 12.
Figure 16:
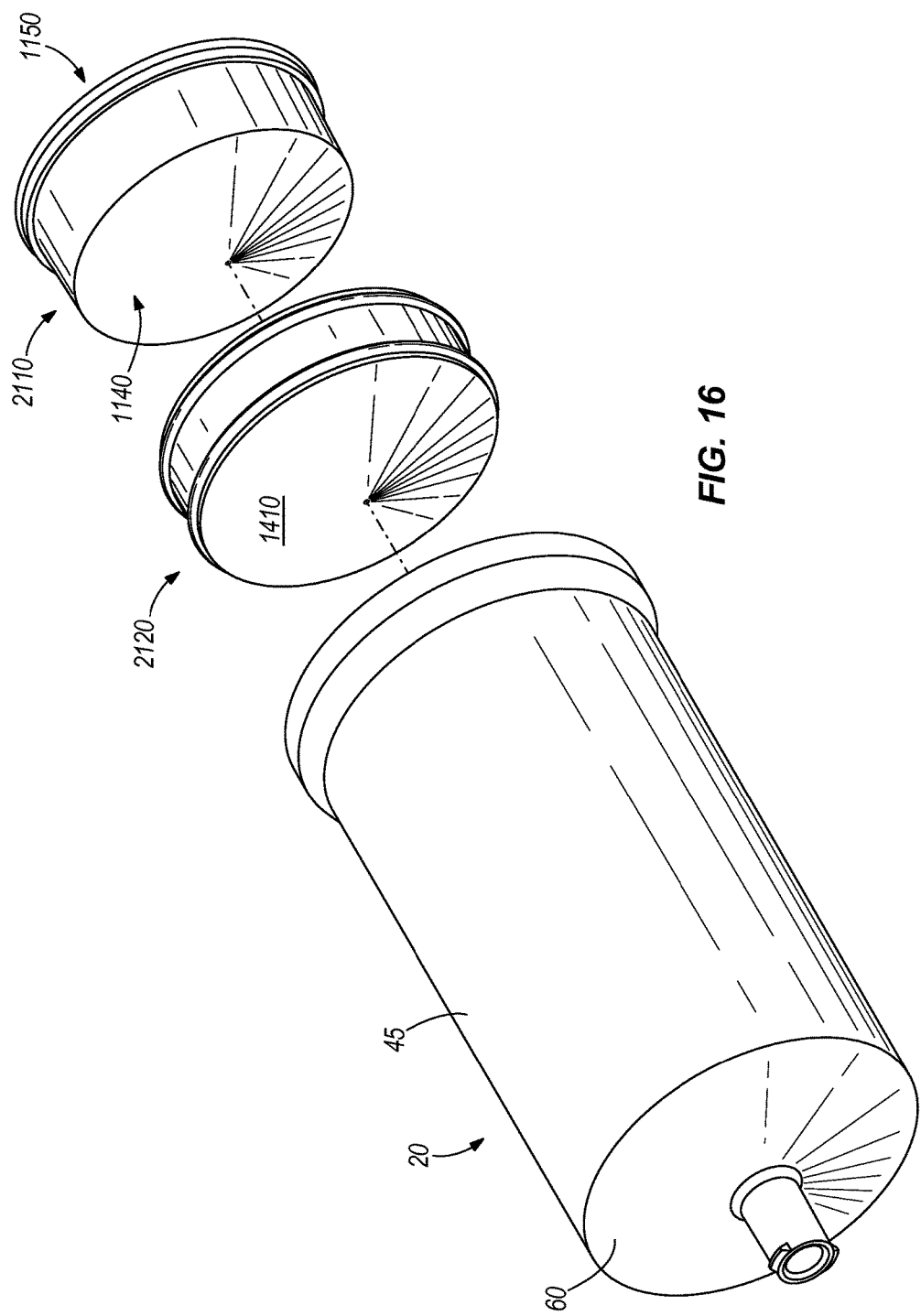
FIG. 16 is an exploded view of a syringe for use in the system illustrated in FIG. 1, the syringe including a barrel, an overmolded seal, and a plunger according to a fourth embodiment of the invention.
Figure 17:
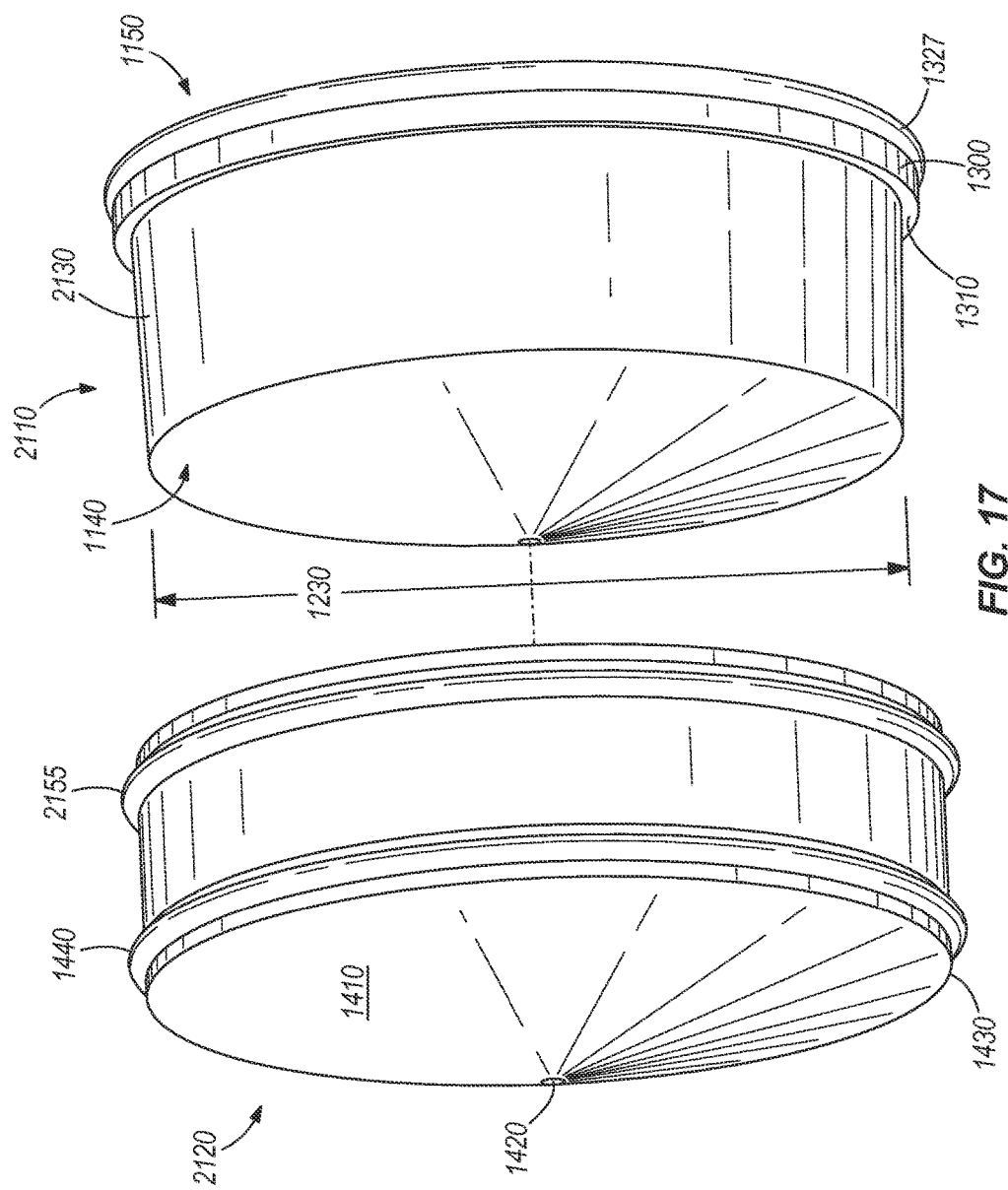
FIG. 17 is an enlarged perspective view of the plunger of FIG. 16.
Figure 18:
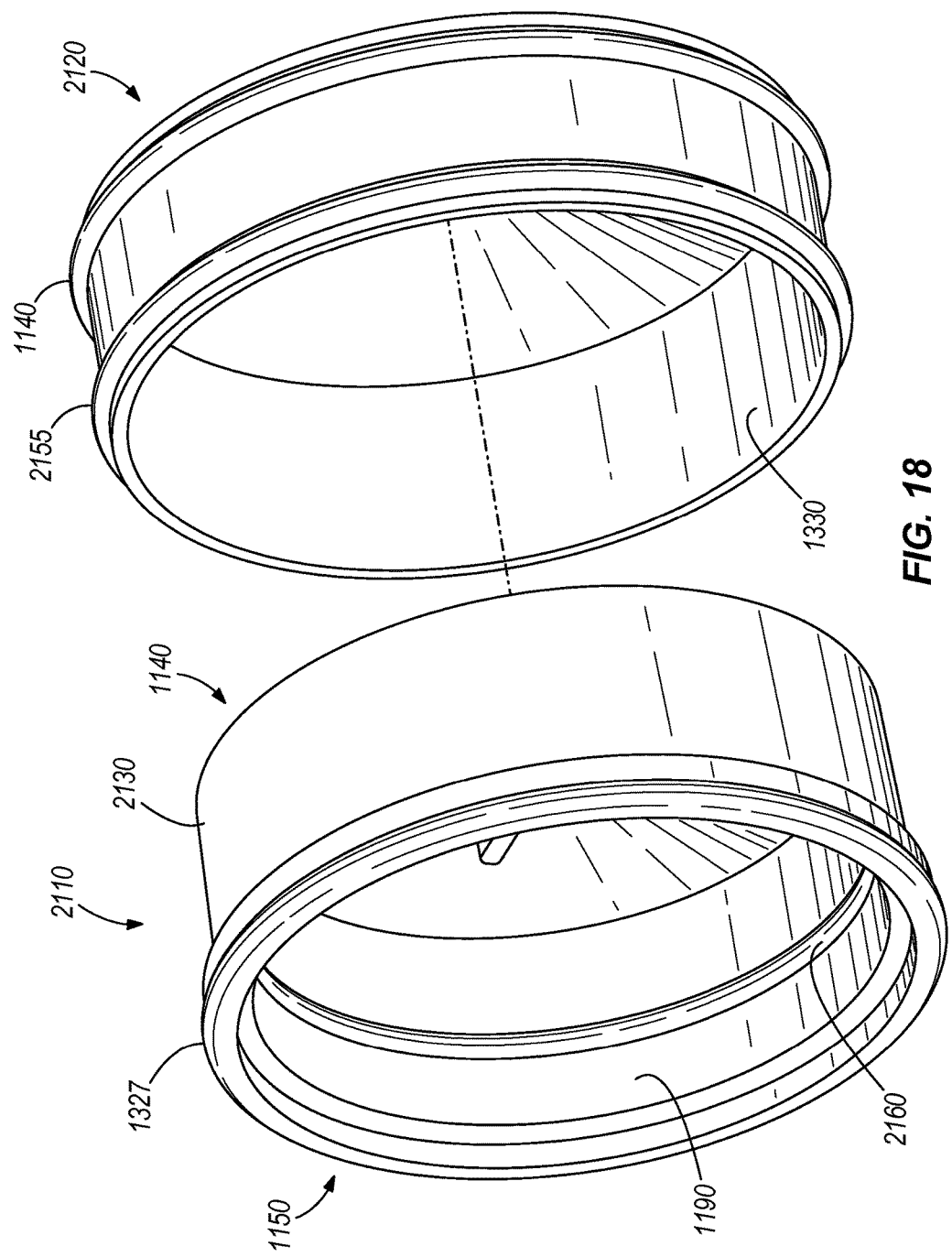
FIG. 18 is an enlarged perspective view of the plunger of FIG. 16 from a perspective different from FIG. 17.
Figure 19:
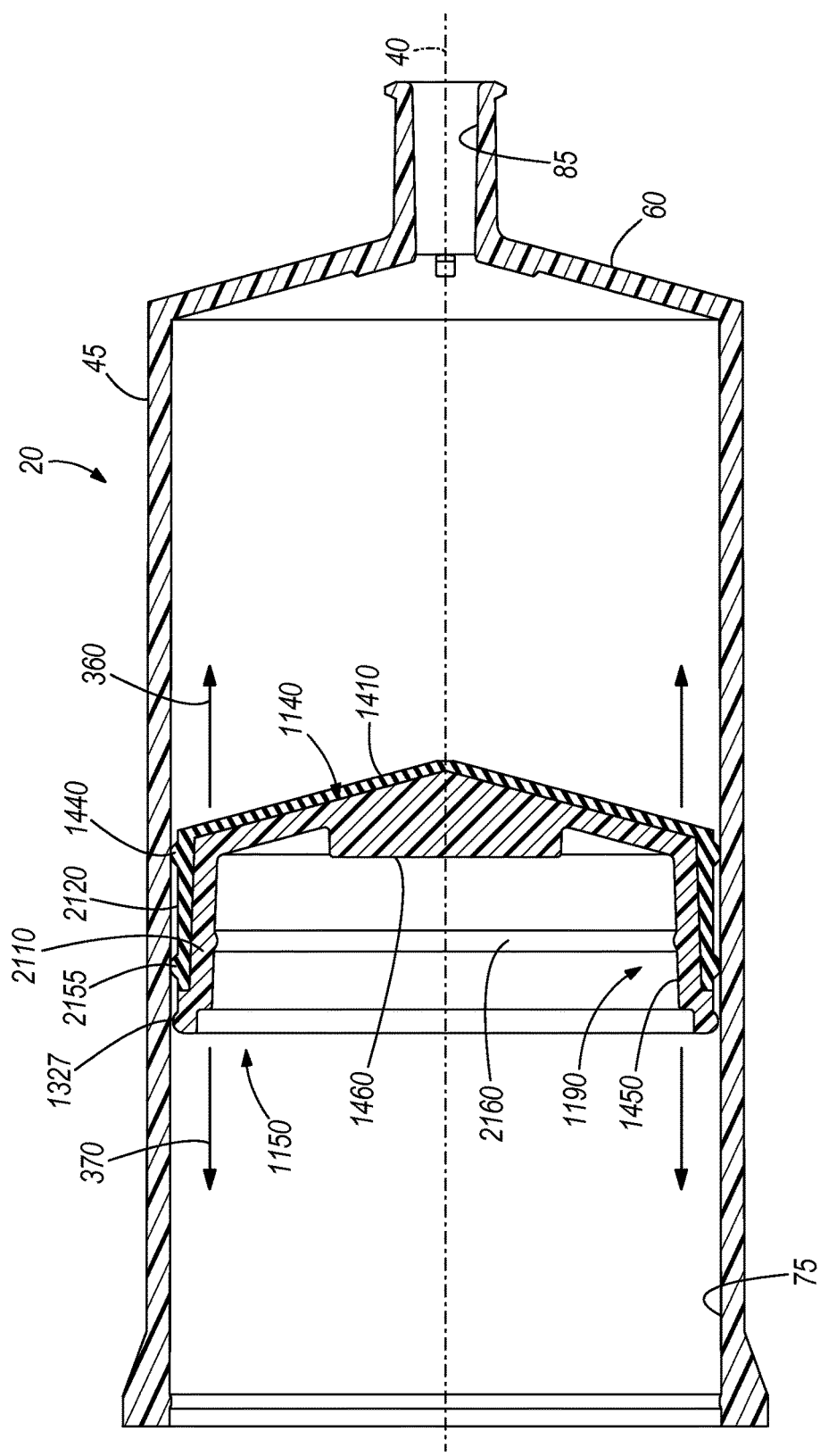
FIG. 19 is a cross-section view of the syringe including the plunger and seal assembly of FIG. 16.

Turning now to FIG. 15, the blind bore 1190 of the plunger 1110 is open at the rear end 1150 of the plunger 1110 and closed at the front end 1140. The blind bore 1190 includes a cylindrical portion 1450, and a plunger seat 1460, which is on the rear-facing side of the head of the plunger 1110. The first embodiment of the overmolded plunger design offers design flexibility to minimize dispensing force, while maintaining good sealing performance over a large temperature range. This concept should also provide cost advantages due to the elimination of assembly steps.

The plunger 1110 is molded with a first shot and the overmolded seal 1120 is molded with a second shot which covers the first shot. This eliminates the first shot's dimensional tolerances from the assembly's tolerance stack, and results in a two piece assembly with reduced variation. This reduced variation can result in reduction of dispensing force for the syringe. Additionally, the overmolded seal 1120 covers any parting lines on the plunger 1110 discussed with respect to the first embodiment above. As a result, the plunger 1110 may be made with the most economical and efficient molding process.

Another advantage is that the TPE and thermoplastic materials have similar thermal expansion, which reduces the dimensional interferences needed to seal over the required thermal range and further reduces the sliding force. Polypropylene in particular has a thermal expansion that is similar to certain TPE's. This design concept also provides the ability to tailor the seal shape for improved sealing. The design may be more cost effective because it eliminates a slow assembly step.

FIGS. 16-19 illustrate a second overmolded version of the plunger assembly, which is a fourth embodiment of the present invention. The second overmolded version includes a plunger 2110 and an overmolded seal 2120. This version does not require a separate o-ring. The plunger 2110 is made of thermoplastic material, such as polypropylene, and the overmolded seal 2120 is made of TPE.

The plunger 2110 is in all respects the same as the plunger 1110 in FIGS. 12-15, except that there is no divider 1180, there is provided a single seal surface 2130 instead of the front seal surface 1160 and rear seal surface 1170, and there is an internal detent ridge 2160 within the blind bore 1190. The detent ridge 2160 can be received within a detent groove on a push rod, so that the detent ridge 2160 resists removal of the push rod from the plunger 2110 unless a sufficient axial separation force is applied. The same reference numbers are used in FIGS. 16-19 for portions of the plunger 2110 that are the same or similar to those of the plunger 1110 in FIGS. 12-15.

The overmolded seal 2120 is a single, integral piece that is molded over the front end 1140 and the seal surface 2130 of the plunger 2110. The overmolded seal 2120 of this embodiment has all the benefits of the overmolded seal 1120 of the previous embodiment. Portions of the overmolded seal 2120 of this embodiment that are the same or substantially similar to those of the previous embodiment are given the same reference numbers as the previous embodiment. This embodiment of the overmolded seal 2120 includes a rear radial wiper 2155 in addition to the front radial wiper 1440. The rear radial wiper 2155 extends radially from the overmolded seal 2120 and extends circumferentially around the plunger 2110 at an axial distance from the front radial wiper 1140. The rear radial wiper 2155 is positioned in about the same axial position as the o-ring 55 of the previous embodiments and performs the same function as the o-ring 55 of the previous embodiments.

Figure 20:
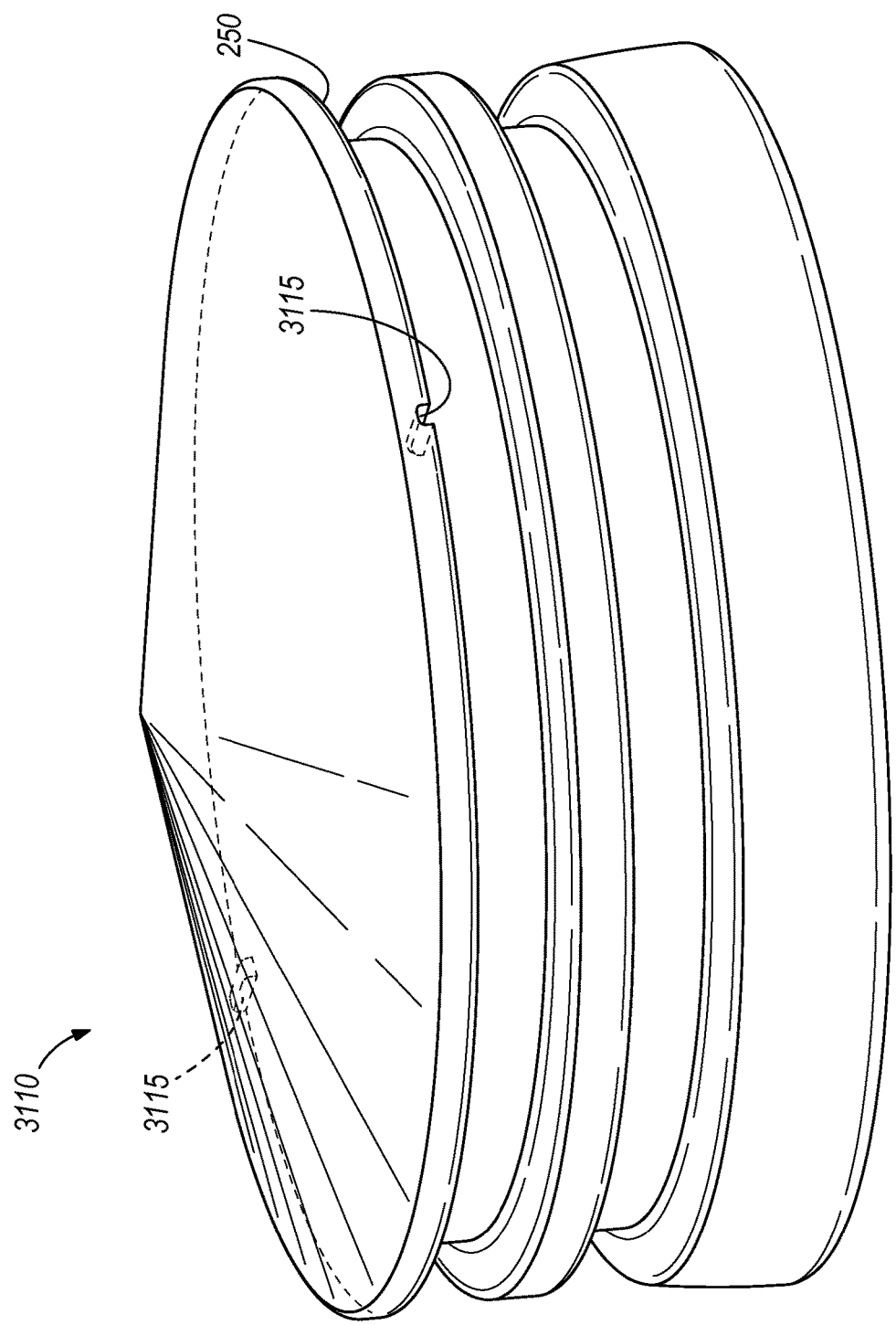
FIG. 20 is a perspective view of another embodiment of the plunger, including venting slots for the front o-ring.
Figure 21:
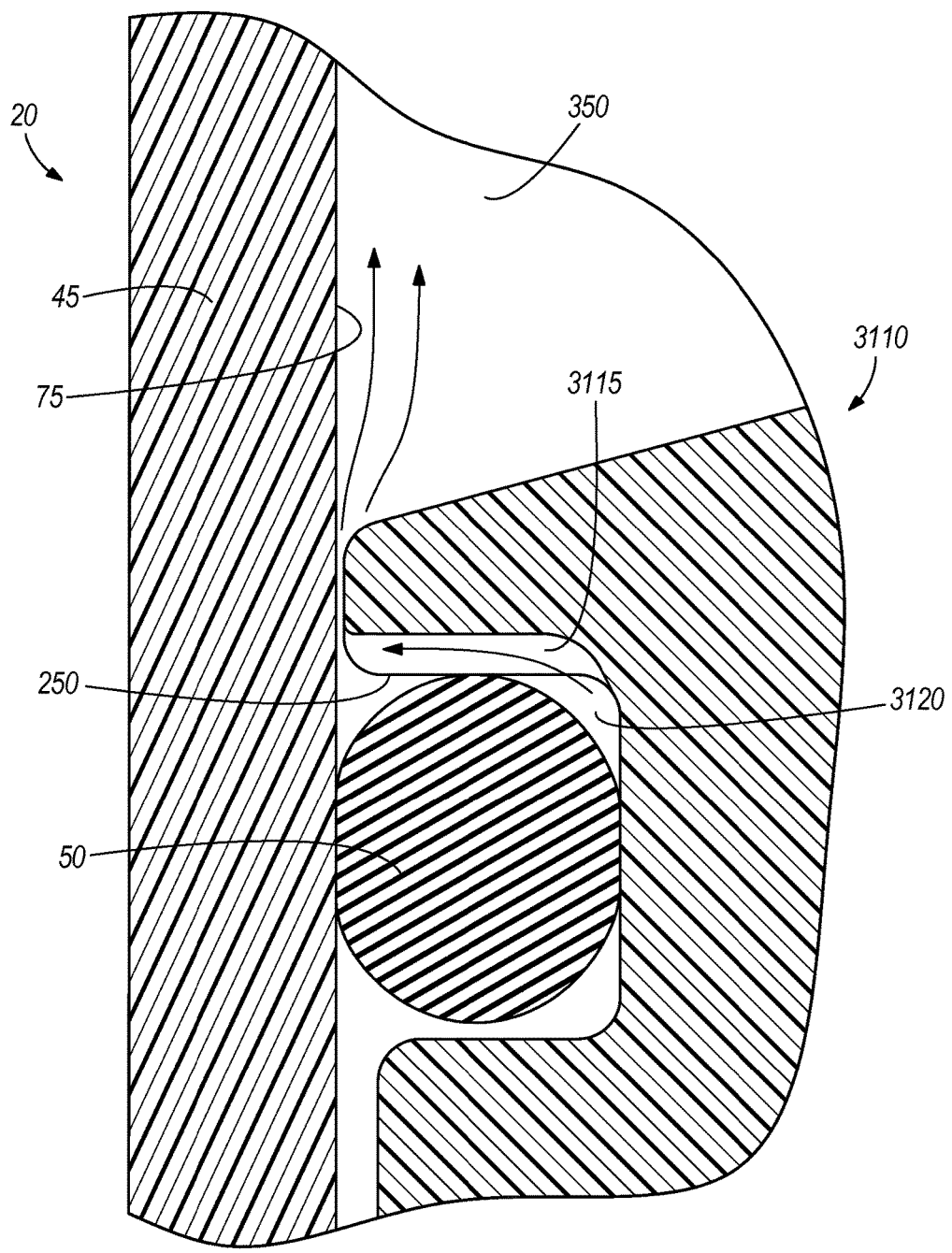
FIG. 21 is an enlarged side section view of the front gland of the plunger illustrated in FIG. 20, with a vacuum being pulled in the syringe barrel.

FIGS. 20 and 21 illustrate another embodiment of the plunger 3110, which is identical in all respects to the plunger 110 in FIGS. 2-5, except for the addition of venting slots 3115. Reference numbers and terminology from the description of plunger 110 will be used for this embodiment for convenience. The venting slots 3115 are integrally molded onto the first rear-facing undercut 250. In the illustrated embodiment, there are a pair of venting slots 3115 that are on diametrically opposed sides of the plunger 3110. The illustrated venting slots 3115 are 0.3 inches deep. The venting slots 3115 communicate between the product chamber 350 and an annular pocket 3120 between the o-ring 50 and the plunger 3110, and more specifically between the front o-ring 50 and the first rear-facing undercut 250. As illustrated in FIG. 21, when a vacuum is pulled in the product chamber 350 of the syringe 20, as during vacuum filling of the syringe 20 with product, air in the annular pocket 3120 is evacuated through the venting slots 3115. When pressure drops in the product chamber 350 during thawing of the product, there will be no air in the pocket 3120 to be drawn into the product chamber 350 to form bubbles.

Figure 23:
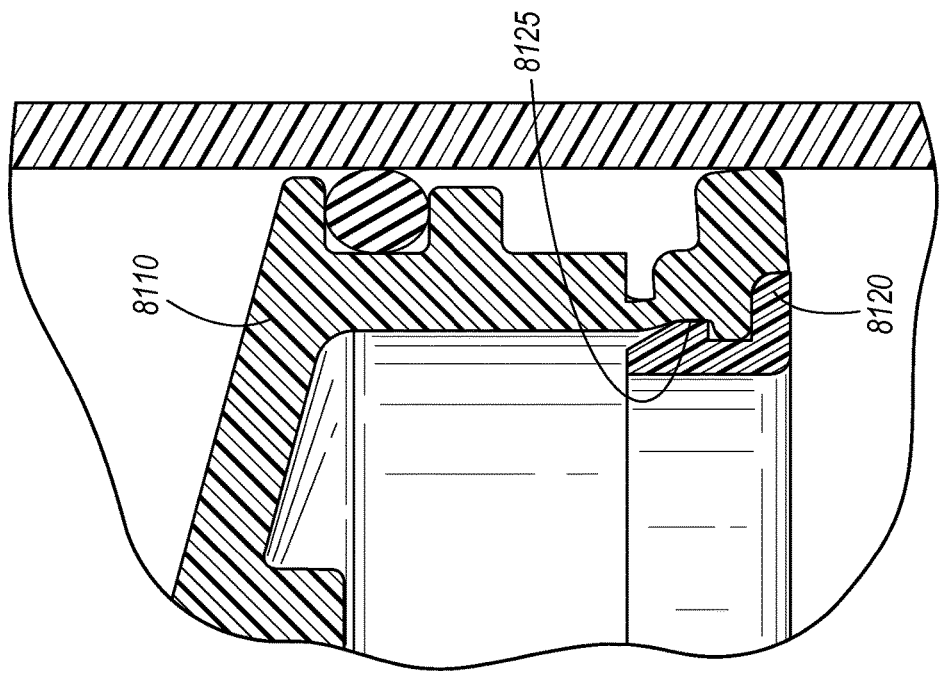
FIG. 23 is a cross sectional view of the plunger of FIG. 22 in the barrel of the syringe.
Figure 22:
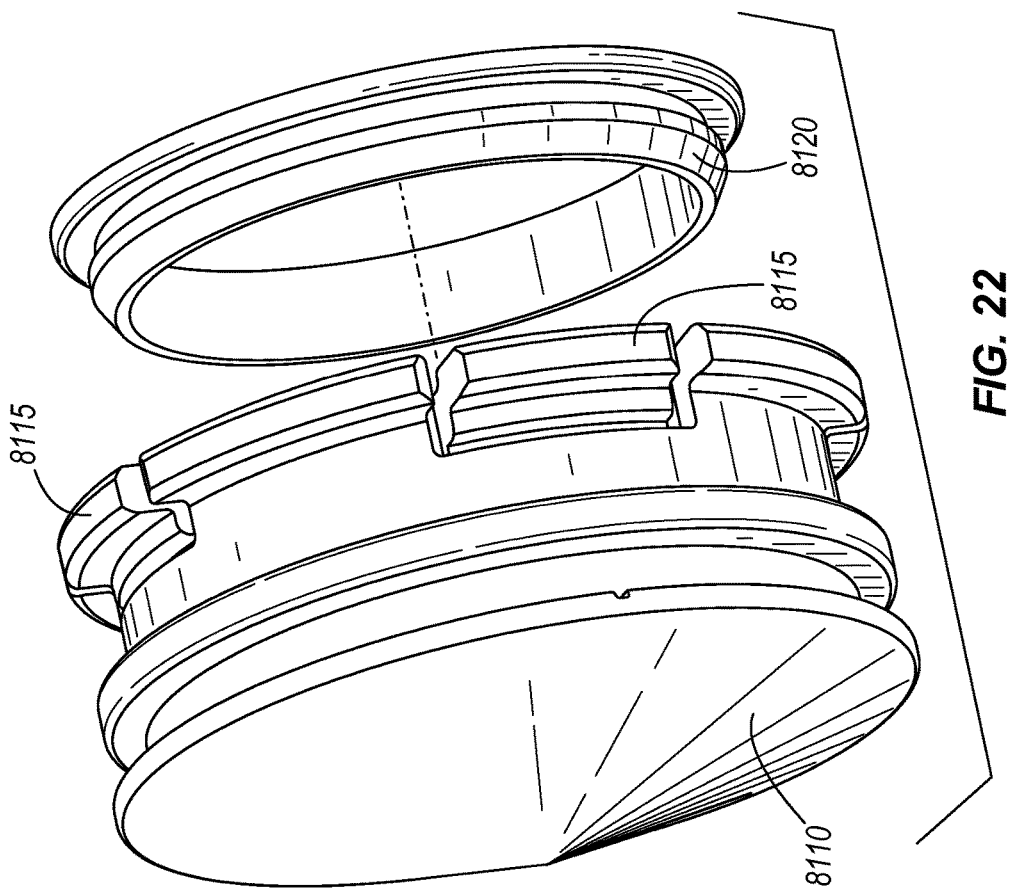
FIG. 22 illustrates another alternative plunger configuration.

FIGS. 22 and 23 illustrate another version of the plunger 8110, which includes a plurality of diametrically-opposed deflectable tabs 8115 and a rigid insert 8120. The rigid insert 8120 is inserted into the plunger body, and expands to deflect the deflectable tabs 8115 radially outwardly. The rigid insert 8120 is ring-shaped so it engages and expands all deflectable tabs 8115. The rigid insert may be a split ring that springs radially outwardly after being inserted into the second end of the plunger 8110, or may be made of a memory shape material that can be compressed for insertion and then expands once inserted. A circumferential groove 8125 may be provided within the plunger body, and the rigid insert 8120 may snap into the groove 8125 to retain the assembly together. Stability is improved by increasing the "wheel base" and ensuring plunger 8110 to syringe contact. The tabs 8115 bear against the inner surface 75 of the barrel 45 to prevent tipping or racking of the plunger 8110.

Figure 25:
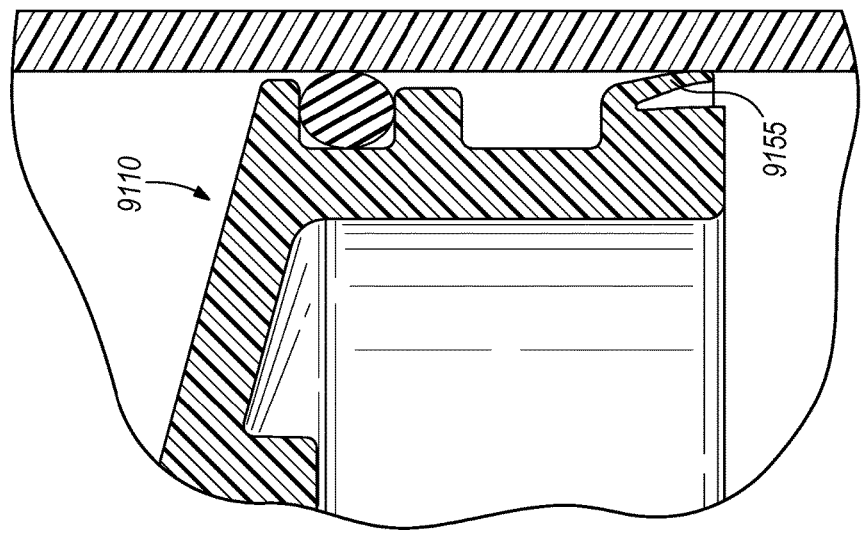
FIG. 25 is a cross sectional view of the plunger of FIG. 24 in the barrel of the syringe.
Figure 24:
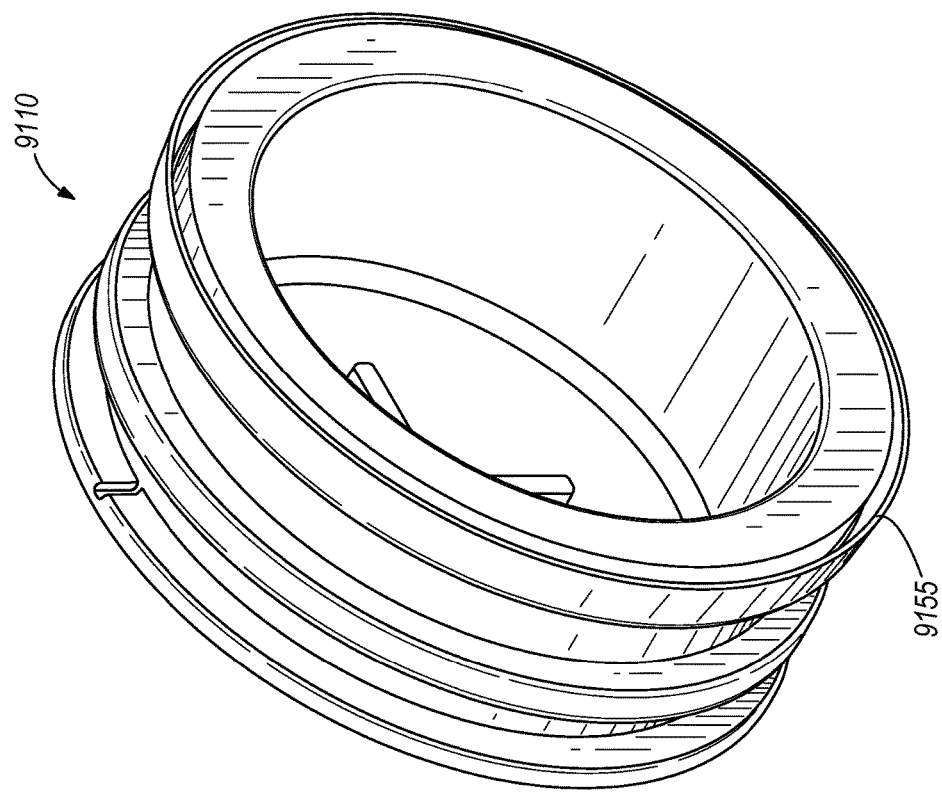
FIG. 24 illustrates another alternative plunger configuration.
Figure 27:
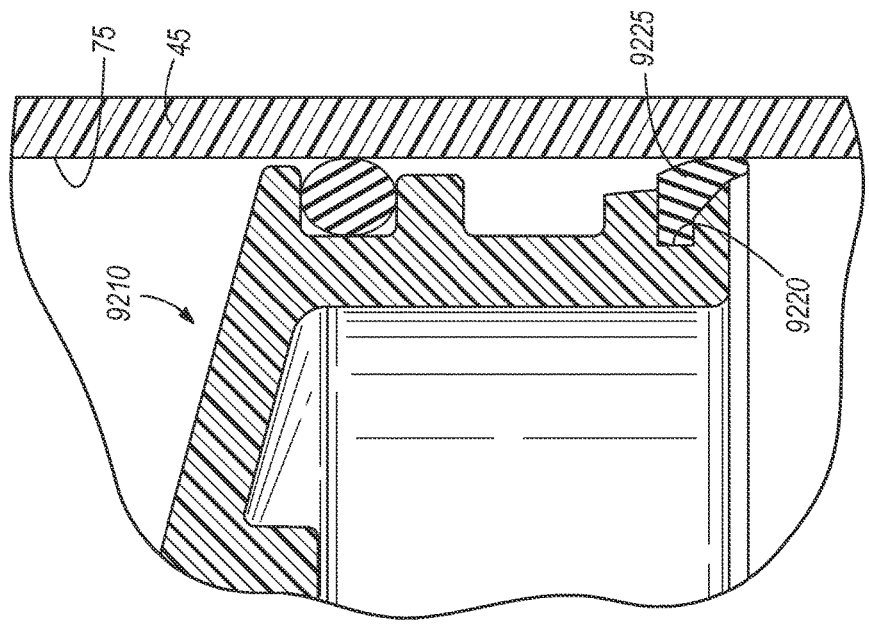
FIG. 27 is a cross sectional view of the plunger of FIG. 26 in the barrel of the syringe.
Figure 26:
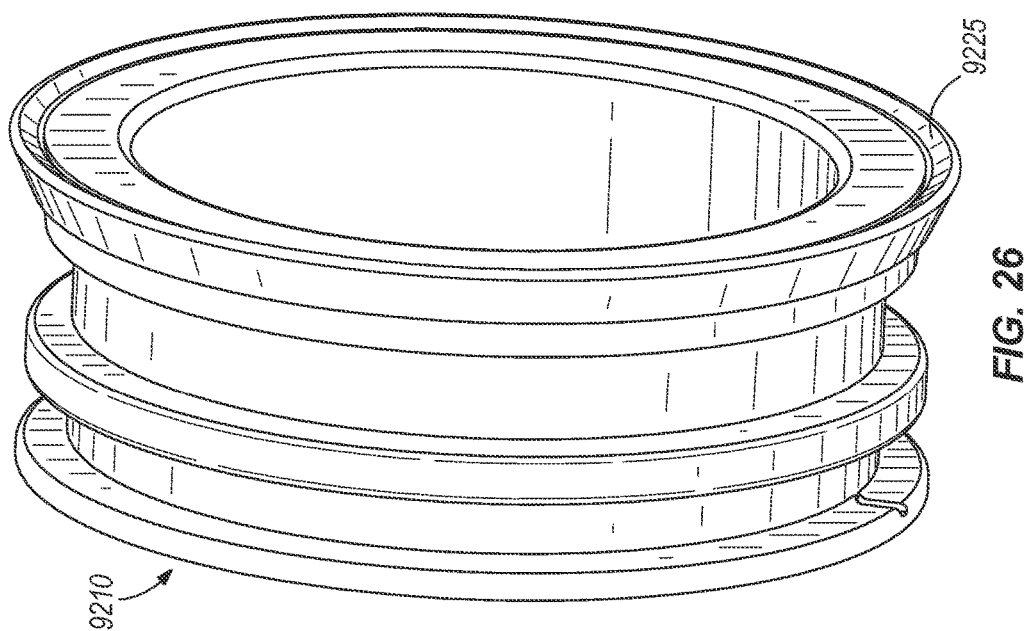
FIG. 26 illustrates another alternative plunger configuration.

FIGS. 24 and 25 illustrate a plunger 9110 in which an integral wiper 9155 replaces the rear o-ring 55. The flexible wiper 9155 is integrated as part of the plunger 9110 which increases stability by widening the "wheel base" of the plunger. FIGS. 26 and 27 illustrate a plunger 9210 which is a variation of the plunger 9110, in which a circumferential slot 9220 is formed in the plunger 9210. A resilient wiper 9225 is inserted into the circumferential slot 9220 and extends radially outwardly into contact with the barrel inner surface 75. The wiper 9225 is attached to the plunger 9210 to increases stability by widening the "wheel base" and ensuring appropriate frictional forces by utilizing a more compliant material.

Thus, the invention provides, among other things, a gas-tight sealing arrangement for a plunger of a syringe, and a method for storing and dispensing product in such a syringe that includes freezing and thawing the syringe and product while maintaining the gas-tight sealing arrangement throughout the process. Various features and advantages of the invention are set forth in the following claims.

What is claimed is:

1. A syringe for use in a drug infusion system, the syringe comprising:
   a barrel having a tapered front end, a rear end, and a cylindrical wall defining an outer surface and an inner surface, the rear end of the barrel being open, and the front end of the barrel including an orifice;
   a plunger within the barrel, the plunger including a continuous contact surface at a front end of the plunger, a rear end of the plunger having an outer cylindrical surface including a tapered outer surface at the rear end of the plunger, a blind bore having an inner cylindrical wall portion defining a continuous even cylindrical surface extending from an entrance of the blind bore to a plunger seat, and a front seal gland extending circumferentially around the plunger between the front end of the plunger and the rear end of the plunger, a rear seal gland extending circumferentially around the plunger between the front seal gland and the rear end of the plunger, the tapered outer surface increasing in diameter from a surface of the rear seal gland to the rear end of the plunger;
   a front o-ring positioned in the front seal gland, and creating a gas-tight seal between the inner surface of the barrel and the plunger; and wherein the front o-ring is sized to maintain the gas tight seal through a temperature change within a temperature range of −25° C. to 40° C.

2. The syringe of claim 1 wherein the front o-ring is surface treated with a lubricant to ensure a gas-tight seal between the front o-ring and the front seal gland.

3. The syringe of claim 1, further comprising:
a rear o-ring made of a rubber compound;
wherein the rear o-ring is positioned in the rear seal gland; and
wherein the rear o-ring creates a gas-tight seal between the inner surface of the barrel and the plunger.

4. The syringe of claim 1, wherein the front end of the plunger defines a head that includes the contact surface;
wherein an outer diameter of the head is slightly smaller than an inner diameter of the barrel such that the head fits within the barrel with close tolerances;
wherein the rear end of the plunger includes an integrally-formed molded ring having a maximum outer diameter that is slightly less than the inner diameter of the barrel such that the integrally-formed molded ring fits within the barrel; and
wherein the head and the integrally-formed molded ring resist tipping of the plunger.

5. The syringe of claim 1, wherein the front o-ring is sized to maintain the gas tight seal through a temperature range of −20° C. to 40° C.

6. The syringe of claim 1, wherein the plunger is molded in a molding process as a single piece; wherein the front seal gland includes a parting line arising from the molding process; wherein a seal between the front o-ring and the front seal gland includes a leak path arising from the parting line; and wherein the front o-ring is surface treated with a lubricant to gas-tightly seal the leak path.

7. The syringe of claim 1, wherein the plunger is molded as a front portion and a rear portion; wherein the front portion is molded with axially-engaging mold portions to form a portion of the front seal gland with no parting lines; and wherein the rear portion is molded with radially-engaging mold portions to form a portion of the front seal gland with parting lines; and wherein the front o-ring is received within the front seal gland with no leak paths between the o-ring and the portion of the front seal gland having no parting lines.

8. The syringe of claim 1, wherein the front seal gland includes a rear-facing undercut surface in front of the o-ring; wherein a pocket is defined between the o-ring and the rear-facing undercut surface of the front seal gland; and wherein the plunger includes a venting slot in the rear-facing undercut surface, the venting slot communicating between the pocket and a product chamber such that air in the pocket is evacuated through the venting slot when a vacuum is applied to the product chamber, wherein the product chamber has a volume defined by the inner surface of the barrel, the front o-ring, and the contact surface.

9. The syringe of claim 8, wherein the pocket is an annular pocket extending around an entire circumference of the front seal gland; wherein the venting slot includes two diametrically opposed venting slots communicating with the annular pocket.

10. The syringe of claim 1, wherein the front o-ring is sized to maintain the gas-tight seal as a product inside a product chamber undergoes a phase change, wherein the product chamber having a volume defined between the inner surface of the barrel, the front o-ring, and the contact surface.

11. The syringe of claim 10, wherein the front o-ring is sized to maintain the gas-tight seal as a product inside the chamber changes volume as it undergoes the phase change.

12. The syringe of claim 1, wherein the contact surface of the plunger is configured to contact the orifice.

13. The syringe of claim 12, wherein an inner diameter of the barrel changes as a result of thermal contraction or thermal expansion.

14. The syringe of claim 1, wherein the plunger seat comprises a step shaped seat.

15. The syringe of claim 1, wherein the inner cylindrical wall portion allows removal of a pushrod upon completion of injection.

16. The syringe of claim 1, wherein the plunger is configured to move rearwardly in response to application of a force to the continuous contact surface while maintaining the gas-tight seal.

* * * * *